US008639008B2

(12) United States Patent
Suri

(10) Patent No.: US 8,639,008 B2
(45) Date of Patent: Jan. 28, 2014

(54) MOBILE ARCHITECTURE USING CLOUD FOR DATA MINING APPLICATION

(75) Inventor: Jasjit S. Suri, Roseville, CA (US)

(73) Assignee: Athero Point, LLC, Roseville, CA (US)

( * ) Notice: Subject to any disclaimer, the term of this patent is extended or adjusted under 35 U.S.C. 154(b) by 154 days.

(21) Appl. No.: 13/449,518

(22) Filed: Apr. 18, 2012

(65) Prior Publication Data
US 2012/0203094 A1 Aug. 9, 2012

Related U.S. Application Data

(63) Continuation-in-part of application No. 12/799,177, filed on Apr. 20, 2010, and a continuation-in-part of application No. 12/802,431, filed on Jun. 7, 2010, now Pat. No. 8,313,437, and a continuation-in-part of application No. 12/896,875, filed on Oct. 2, 2010, now Pat. No. 8,485,975, and a continuation-in-part of application No. 12/960,491, filed on Dec. 4, 2010, and a continuation-in-part of application No. 13/053,971, filed on Mar. 22, 2011, and a continuation-in-part of application No. 13/077,631, filed on Mar. 31, 2011, and a continuation-in-part of application No. 13/107,935, filed on May 15, 2011, and a continuation-in-part of application No. 13/219,695, filed on Aug. 28, 2011, and a continuation-in-part of application No. 13/253,952, filed on Oct. 5, 2011, now Pat. No. 8,532,360, and a continuation-in-part of application No. 13/407,602, filed on Feb. 28, 2012, now abandoned, and a continuation-in-part of application No. 13/412,118, filed on Mar. 5, 2012.

(60) Provisional application No. 61/525,745, filed on Aug. 20, 2011.

(51) Int. Cl.
G06K 9/00 (2006.01)

(52) U.S. Cl.
USPC .......................................... 382/131

(58) Field of Classification Search
USPC ............ 382/131; 600/479, 481, 483; 700/776
See application file for complete search history.

(56) References Cited

U.S. PATENT DOCUMENTS

| 5,343,867 | A | 9/1994 | Shankar |
| 5,734,739 | A | 3/1998 | Sheehan et al. |
| 6,132,373 | A | 10/2000 | Ito et al. |
| 6,251,072 | B1 | 6/2001 | Ladak et al. |
| 6,267,728 | B1 | 7/2001 | Hayden |
| 6,347,152 | B1 | 2/2002 | Shinagawa et al. |
| 6,597,937 | B2 | 7/2003 | Liu et al. |
| 6,614,453 | B1 | 9/2003 | Suri et al. |
| 6,718,055 | B1 | 4/2004 | Suri |

(Continued)

FOREIGN PATENT DOCUMENTS

WO WO03042921 A 5/2003

Primary Examiner — Gregory F Cunningham

(57) ABSTRACT

Three tier architecture for image-based diagnosis and monitoring application using Cloud is described. The presentation layer is run on the tablet (mobile device), while the business and persistence layer runs on a single cloud or distributed on different Clouds in a multi-tenancy and multi-user application. Such architecture is used for automated data mining application for computing (a) cardiovascular risk, stroke risk using IMT measurement, plaque characterization, (b) computing diagnostic index for benign vs. malignant tissue for ovarian cancer classification (c) benign vs. malignant tissue characterization for prostate cancer and (d) classification of fatty liver disease vs. normal cases. The Architecture is for data mining application.

20 Claims, 16 Drawing Sheets

(56) References Cited

U.S. PATENT DOCUMENTS

| | | |
|---|---|---|
| 6,785,409 B1 | 8/2004 | Suri |
| 6,813,373 B1 | 11/2004 | Suri et al. |
| 6,817,982 B2 | 11/2004 | Fritz et al. |
| 6,835,177 B2 | 12/2004 | Fritz et al. |
| 6,842,638 B1 | 1/2005 | Suri et al. |
| 6,845,260 B2 | 1/2005 | Liu et al. |
| 6,987,568 B2 | 1/2006 | Dana |
| 7,020,314 B1 | 3/2006 | Suri et al. |
| 7,024,027 B1 | 4/2006 | Suri et al. |
| 7,074,187 B2 | 7/2006 | Selzer et al. |
| 7,110,000 B2 | 9/2006 | Zhang et al. |
| 7,149,368 B2 | 12/2006 | Tong et al. |
| 7,161,601 B2 | 1/2007 | Zhang et al. |
| 7,272,241 B2 | 9/2007 | Demi et al. |
| 7,340,083 B2 | 3/2008 | Yuan et al. |
| 7,353,117 B2 | 4/2008 | Yuan et al. |
| 7,376,253 B2 | 5/2008 | Spreeuwers et al. |
| 7,639,261 B2 | 12/2009 | Sekine et al. |
| 7,657,299 B2 | 2/2010 | Huizenga et al. |
| 7,680,330 B2 | 3/2010 | Leung |
| 7,686,764 B2 | 3/2010 | Watanabe et al. |
| 2003/0053669 A1 | 3/2003 | Suri et al. |
| 2003/0236460 A1 | 12/2003 | Ma et al. |
| 2004/0243365 A1 | 12/2004 | Yuan et al. |
| 2005/0042222 A1* | 2/2005 | Yamamoto et al. ........ 424/146.1 |
| 2005/0043614 A1 | 2/2005 | Huizenga et al. |
| 2005/0119555 A1 | 6/2005 | Fritz et al. |
| 2006/0064016 A1 | 3/2006 | Demi et al. |
| 2006/0241465 A1 | 10/2006 | Huennekens et al. |
| 2007/0003116 A1 | 1/2007 | Yuan et al. |
| 2007/0038061 A1 | 2/2007 | Huennekens et al. |
| 2007/0269086 A1 | 11/2007 | Kerwin et al. |
| 2007/0287897 A1 | 12/2007 | Faris |
| 2008/0009702 A1 | 1/2008 | Liu et al. |
| 2008/0051658 A1 | 2/2008 | Demi et al. |
| 2008/0080755 A1 | 4/2008 | Payonk et al. |
| 2008/0095422 A1 | 4/2008 | Suri et al. |
| 2008/0145841 A1* | 6/2008 | Libutti et al. .................... 435/6 |
| 2008/0171939 A1 | 7/2008 | Ishihara |
| 2008/0221446 A1 | 9/2008 | Washburn et al. |
| 2008/0269595 A1 | 10/2008 | Wong |
| 2008/0274457 A1 | 11/2008 | Eng et al. |
| 2008/0316374 A1 | 12/2008 | Koike et al. |
| 2009/0028793 A1 | 1/2009 | Neri et al. |
| 2009/0252395 A1* | 10/2009 | Chan et al. .................... 382/131 |
| 2010/0060644 A1 | 3/2010 | Elie et al. |
| 2010/0081931 A1 | 4/2010 | Destrempes et al. |

* cited by examiner

MOBILE ARCHITECTURE USING CLOUD FOR DATA MINING APPLICATION

PRIORITY APPLICATIONS

This is a continuation-in-part patent application of co-pending patent application Ser. No. 12/799,177; filed Apr. 20, 2010 by the same applicant. This is also a continuation-in-part patent application of co-pending patent application Ser. No. 12/802,431; filed Jun. 7, 2010 by the same applicant. This is also a continuation-in-part patent application of co-pending patent application Ser. No. 12/896,875; filed Oct. 2, 2010 by the same applicant. This is also a continuation-in-part patent application of co-pending patent application Ser. No. 12/960,491; filed Dec. 4, 2010 by the same applicant. This is also a continuation-in-part patent application of co-pending patent application Ser. No. 13/053,971; filed Mar. 22, 2011 by the same applicant. This is also a continuation-in-part patent application of co-pending patent application Ser. No. 13/077,631; filed Mar. 31, 2011 by the same applicant. This is also a continuation-in-part patent application of co-pending patent application Ser. No. 13/107,935; filed May 15, 2011 by the same applicant. This is also a continuation-in-part patent application of co-pending patent application Ser. No. 13/219,695; filed Aug. 28, 2011 by the same applicant. This is also a continuation-in-part patent application of co-pending patent application Ser. No. 13/253,952; filed Oct. 5, 2011 by the same applicant. This is also a continuation-in-part patent application of co-pending patent application Ser. No. 13/407,602; filed Feb. 28, 2012 by the same applicant. This is also a continuation-in-part patent application of co-pending patent application Ser. No. 13/412,118; filed Mar. 5, 2012 by the same applicant. This present patent application draws priority from the referenced co-pending patent applications. This present patent application also draws priority from the provisional patent application Ser. No. 61/525,745; filed Aug. 20, 2011 by the same applicant. The entire disclosures of the referenced co-pending patent applications and the provisional patent application are considered part of the disclosure of the present application and are hereby incorporated by reference herein in its entirety.

TECHNICAL FIELD

This application relates to a method and system for use with data processing and imaging systems, according to one embodiment, and more specifically, for a mobile architecture using cloud for data mining application.

BACKGROUND

Imaging-based technologies have been active for over a century and today the same imaging-based technologies are used electronically for creating pictures of the human body and examining it. Majority of these imaging modalities are non-invasive and painless. Depending upon the symptoms of the patient's disease, a physician will choose a type of the imaging modality, its diagnosis, treatment and monitoring. Some of the most famous medical imaging modalities are Ultrasound, X-ray, MR, CT, PET, SPECT and now more molecular and cellular level. These imaging modalities are conducted by the radiologist or a technologist who are well trained to operate and know the safety rules.

The important of imaging-based techniques for diagnosis, treatment, monitoring is increasing day-by-day. Thus more and more body images are generated every day. Hospitals and health care providers are generating image data at an alarming rate. There is no doubt that one has to design complex medical imaging software for diagnosis, treatment and monitoring, but it is becoming challenging to access these data in this age of the world. Storage of the medial images is one issue and how to access this data for decision making such as diagnosis, treatment and monitoring is another issue.

BRIEF SUMMARY AND THE OBJECTS OF THE DISCLOSED EMBODIMENTS

This application is a novel method (called AtheroMobile™) and presents three tier architecture for image-based diagnosis and monitoring application using cloud. The presentation layer is run on the tablet (mobile device), while the business and persistence layer runs on the cloud or a set of clouds. The business and presentation layers can be in one cloud or multiple clouds. Further, the system can accommodate multiple users in this architecture set-up with multiple tenancies. An example is AtheroCloud™ application compatible with Windows XP and Windows 7 for the use on a personal computer for the automatic measurement of the intima-media thickness (IMT) of the common carotid artery (CCA). AtheroCloud™ application is designed to help delineate the lumen-intima (LI) and media-adventitia (MA) borders of the distal wall in the carotid ultrasound image by: i) automatically recognizing the carotid artery and tracing the far adventitia layer (ADF) in the 2-dimensional carotid ultrasound image, and ii) automatically tracing the boundaries between the lumen-intima and media-adventitia.

Data access from remote locations has become important day-by-day in this high information technology world. Due to this, now Cloud-based imaging can provide solution to such challenges. Even though, HIPPA or security or data ownership technologies are evolving, but the pros of Cloud-based technologies have outweighed the cons.

The Cloud-based technology offers, the first one is pricing. Cloud-based processing is less expensive due to low storage cost. Additional benefit is that if one uses Cloud for Software as a Service (SaaS) application, the storage cost can be free.

Another advantage of Cloud-based processing is the capacity to handle. Compared to costs for the local processing when the data storage requirements are changing dynamically, Cloud-based capacity may be advantageous. Expansion possibility is easy to handle. Emergency storage requirements may also less challenging to handle in Cloud-based processing.

Another major advantage is the disaster recovery. One needs regular backups and maintenance; this can be avoided in the Cloud-based processing.

Having discussed the benefits of Cloud-based processing, it is thus important on how to use Cloud-based services for applications which short time to run applications. This innovative application is about the architecture is designed for medical imaging applications, such as cardiovascular, prostate cancer, ovarian cancer, thyroid cancer and liver cancer. Today's medical based applications do not just require viewing of the images, but also processing business layers for doctors to get the clinical information such as diagnosis, treatment support and monitoring. Thus the main requirement in today's Cloud-based processing is how to build medical imaging architectures which can benefit from Cloud-based processing.

Now that hand held devices have come into the world such as iPad, Samsung tablets or iPhones, it is thus important to understand how to build medical imaging architectures which has several tiers or layers in their architectural designs. This innovative application demonstrates an imaging-based architecture utilizing the Cloud-based processing. The application shows coverage for vascular market or Cardiac market, gynecological market, prostate cancer market and liver cancer market, but is extendable to other anatomies as well.

In view of the foregoing, it is a primary object of the present invention to provide a novel method and apparatus for automated mobile data mining from ultrasound images for diagnostic and monitoring application and further providing extensions to MR or CT images and in general to any other imaging-based data mining application.

It is another object of the present invention to develop a mobile-based architecture which can process images by distributing components of the architecture in different Clouds, but same physical location.

It is another object of the present invention to develop a data mining architecture having the business layer in one Cloud while running the Persistence Layer in another Cloud, not necessarily in the same physical location.

It is another object of the present invention to develop an image-based data mining Cloud-based application which can have multiple-tenants and multiple-users. This data mining application can be where the Business layer is for cardiovascular application (such as IMT measurement, IMTV measurement, Plaque Characterization for Symptomatic vs. Asymptomatic classification of plaque, Stroke Risk computation, and monitoring stroke risk), or urology application such as benign vs. malignant tissue prostate tissue classification for prostate cancer, or gynecological application for classification of ovarian cancer or benign vs. malignant thyroid cancer for endocrinology application or for liver application—such as a classification of fatty liver disease (FLD) compared to normal liver.

It is another object of the present invention to provide different configuration options in the Business Layer controlled by the Presentation Layer, where the Presentation Layer can control wirelessly different configurations. Each configuration can be another scientific method for generation of clinical information.

It is another object of the present invention to provide multi-tenancy for data mining applications using distributed architectures, where data mining application can be Business layer for (a) cardiovascular application (such as IMT measurement, IMTV measurement, Plaque Characterization for Symptomatic vs. Asymptomatic classification of plaque, Stroke Risk computation, and monitoring stroke risk); (b) prostate cancer application (such as benign vs. malignant prostate tissue classification or characterization for prostate cancer); (c) ovarian cancer tissue characterization and classification; or (d) thyroid cancer application (such as benign vs. malignant thyroid tissue classification or characterization for thyroid cancer); or (e) classification of liver tissue such as Fatty Liver Disease.

It is another object of the present invention to provide multi-tenancy for data mining applications using distributed architectures, where multi-tenancy can be using different imaging modality like MRI, CT, Ultrasound or a combination of these for fusion. The multi-tenancy set-up has data mining application where Business layer is: (a) cardiovascular application (such as IMT measurement, IMTV measurement, Plaque Characterization for Symptomatic vs. Asymptomatic classification of plaque, Stroke Risk computation, and monitoring stroke risk); (b) prostate cancer application (such as benign vs. malignant prostate tissue classification or characterization for prostate cancer); (c) ovarian cancer tissue characterization and classification; or (d) thyroid cancer application (such as benign vs. malignant thyroid tissue classification or characterization for thyroid cancer); or (e) classification of liver tissue such as Fatty Liver Disease.

It is another object of the present invention to provide data mining applications using distributed architectures, where the presentation layer can be hand-held device like iPhone, iPad, Samsung Tablet or notebook or laptop or desktop and data mining application can be for (for (a) cardiovascular application (such as IMT measurement, IMTV measurement, Plaque Characterization for Symptomatic vs. Asymptomatic classification of plaque, Stroke Risk computation, and monitoring stroke risk); (b) prostate cancer application (such as benign vs. malignant prostate tissue classification or characterization for prostate cancer); (c) ovarian cancer tissue characterization and classification; or (d) thyroid cancer application (such as benign vs. malignant thyroid tissue classification or characterization for thyroid cancer); or (e) classification of liver tissue such as Fatty Liver Disease.

It is another object of the present invention to provide data mining applications where Business layer for (a) cardiovascular application (such as IMT measurement, IMTV measurement, Plaque Characterization for Symptomatic vs. Asymptomatic classification of plaque, Stroke Risk computation, and monitoring stroke risk); (b) prostate cancer application (such as benign vs. malignant prostate tissue classification or characterization for prostate cancer); (c) ovarian cancer tissue characterization and classification; or (d) thyroid cancer application (such as benign vs. malignant thyroid tissue classification or characterization for thyroid cancer); or (e) classification of liver tissue such as Fatty Liver Disease, such that it can process the B-mode ultrasound or RF-mode ultrasound images.

It is another object of the present invention to provide mobile data mining application where Business layer can predict the Cardiovascular Risk by linking the HbA1c score for Diabetic patients. Such a class of algorithms can be categorized under AtheroEdgeLink™.

It is another object of the present invention to provide data mining applications where Business layer can predict the Cardiovascular Risk by linking the Syntax Score (computed using Coronary Angiography) for patients having Coronary Artery Disease with automated IMT measurement in Carotid Ultrasound Images. Such a class of algorithms can be categorized under AtheroEdgeLink™.

It is another object of the present invention to provide mobile data mining application where Business layer can be a 2D processing unit or a 3D processing unit.

It is another object of the present invention to provide mobile data mining application where Business layer can be a 2D processing unit or a 3D processing unit for diagnostic and monitoring application with different configuration options for the Business Layer.

It is another object of the present invention to provide mobile data mining application where Business layer can be a 2D processing unit or a 3D processing unit for diagnostic and monitoring application with different configuration options for the Business Layer, where these applications use training-based systems.

BRIEF DESCRIPTION OF THE DRAWINGS

The various embodiments is illustrated by way of example, and not by way of limitation, in the figures of the accompanying drawings in which.

DETAILED DESCRIPTION OF THE PREFERRED EMBODIMENTS

Figure 1:
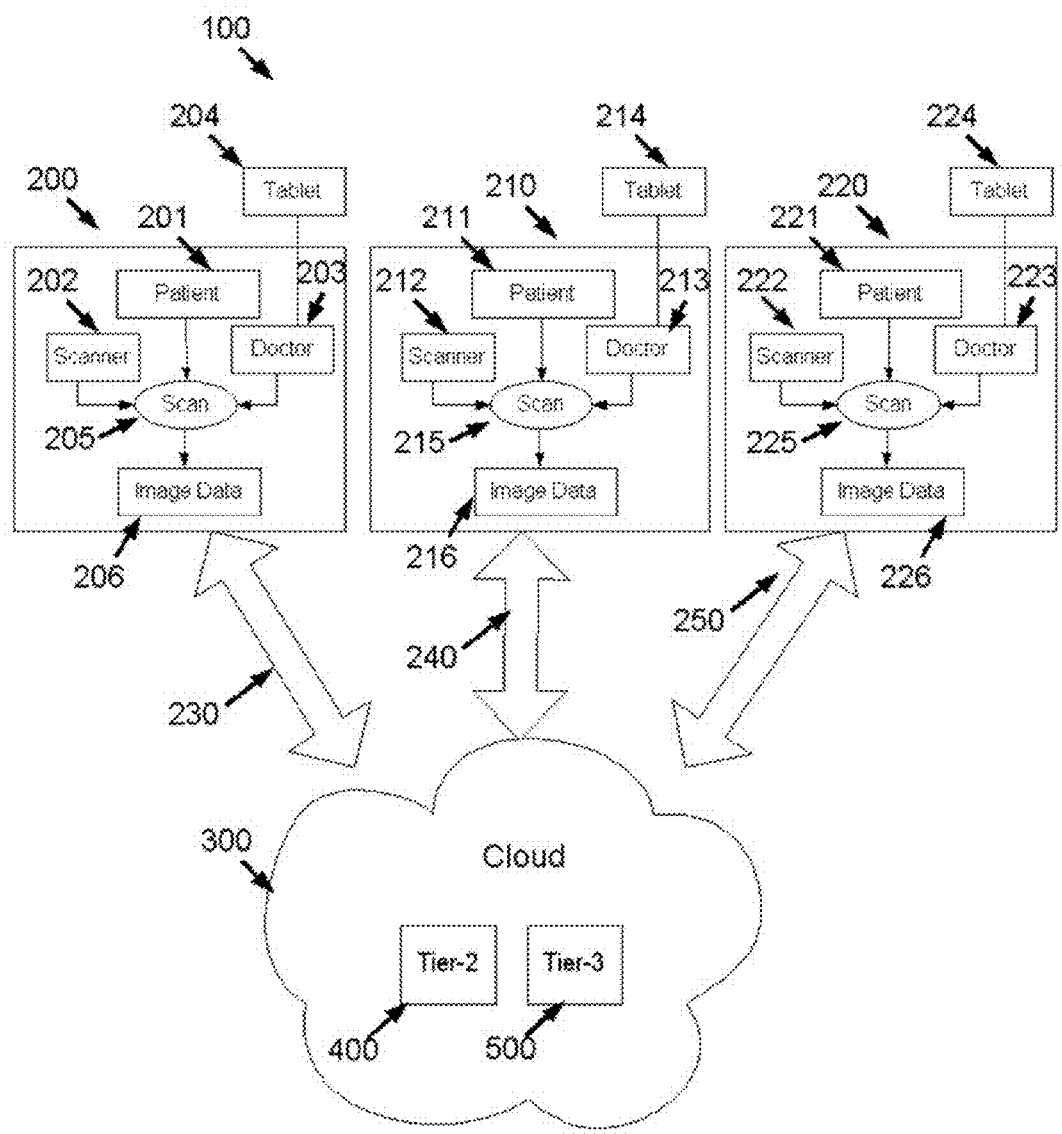
FIG. 1 illustrates an example of mobile architecture system.

FIG. 1 show the example embodiment 100 of the architecture where the application is split into three tiers: Tier-1 is the presentation layer and Tier-2 and Tier-3 are the business layer and persistence layers. The main advantage of this data mining applications which require large space and still be able to maintain near real-time applications. Another key advantage of such a architecture is the ability to decouple business and persistence layers in different clouds and still be able to execute data mining applications. An example embodiment can be for vascular application, men's urology application, women's urology application, breast mammography application, liver application, cardiac application, kidney application. Blocks 200, 210 and 220 represent different health care systems connected to the cloud 300 having architectures 400 and 500 called as Tier-2 and Tier-3. The connection between the health care systems 200, 210 and 220 to the Cloud 300 is shown using links 230, 240 and 250, respectively. Inside each health care system run the patient data collection systems using the scanners: 205, 215, and 225. These scanners collected image data on the patient 201, 211 and 221 using the scanners 202, 212 and 222, respectively. The physician or technologist is shown in FIGS. 203, 213 or 223. The image data collected is shown in the blocks 206, 216 and 226 respectively, which is sent to the cloud 300 using the links 230, 240 and 250, respectively. This application uses automated data mining business layer 400 and persistence layer 500 in the cloud 300. The hand-held devices 204, 214 and 224 (Tier-1) are used for running the data mining applications receding in the Cloud 300. These hand-held devices can be iPad or a Tablet or a notebook or a laptop. This application uses the architecture for a) cardiovascular application (such as IMT measurement, IMTV measurement, Plaque Characterization for Symptomatic vs. Asymptomatic classification of plaque, Stroke Risk computation, and monitoring stroke risk); (b) prostate cancer application (such as benign vs. malignant prostate tissue classification or characterization for prostate cancer); (c) ovarian cancer tissue characterization and classification; or (d) thyroid cancer application (such as benign vs. malignant thyroid tissue classification or characterization for thyroid cancer); or (e) classification of liver tissue such as Fatty Liver Disease, such that it can process the B-mode ultrasound or RF-mode ultrasound images.

Figure 2:
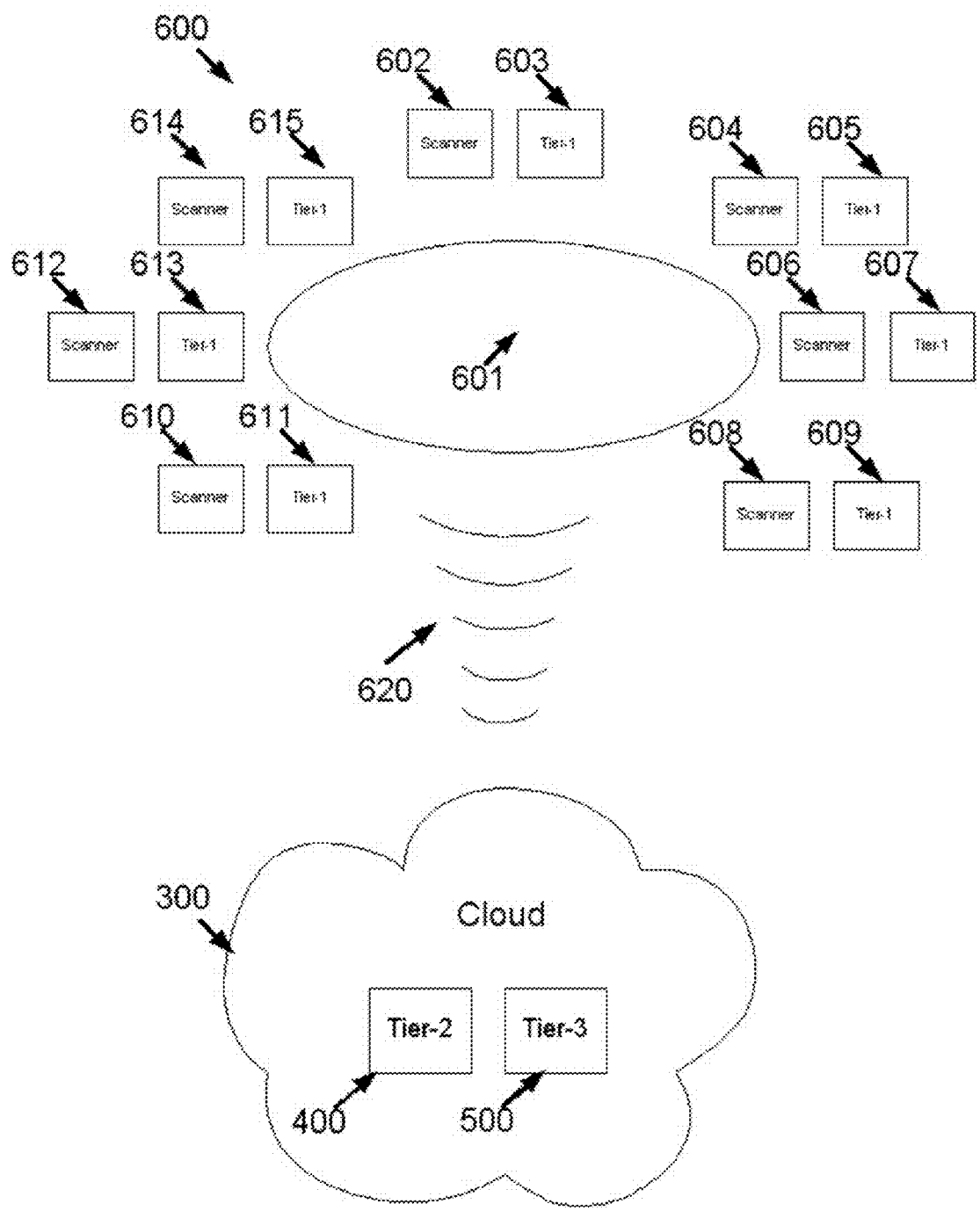
FIG. 2 shows an illustrative example of multi-user application using cloud.

FIG. 2 shows the example embodiment 600 where multiple healthcare providers having multiple Tier-1's and are connected to the Cloud running the Tier-2 and Tier-3. For example 602 and 603 represent one health care system where the Tier-1 block 603 is interacting with the Cloud 300 which has the Tier-2, block 400 and Tier-3, block 500 using a wireless system. Similar pairs can be blocks 604 and 605 representing a scanner and a presentation layer in combination. A cyclic order of such combination representing several healthcare systems can be 606 and 607; 608 and 609; 610 and 611; 612 and 613; 614 and 615, respectively. Those skilled in the art can add more clients in such a cyclic framework. The wireless signals are represented by 620 which are sending the client signals to the Tier-2 which in return can store the intermediate results in Tier-3. Using this architecture, one can also send signal from Tier-1 such as (603, 605, 609, 611,613 and 615) to Tier-3 receding in the Cloud 300. The main advantage of such a system is the decoupling of the Tier-1 from Tier-2 and Tier-3. Those skilled in the art of using client-server model, can reside the Tier-2 on one server and Tier-3 in another sever or both Tier-2 and Tier-3 in the same Cloud.

Figure 3:
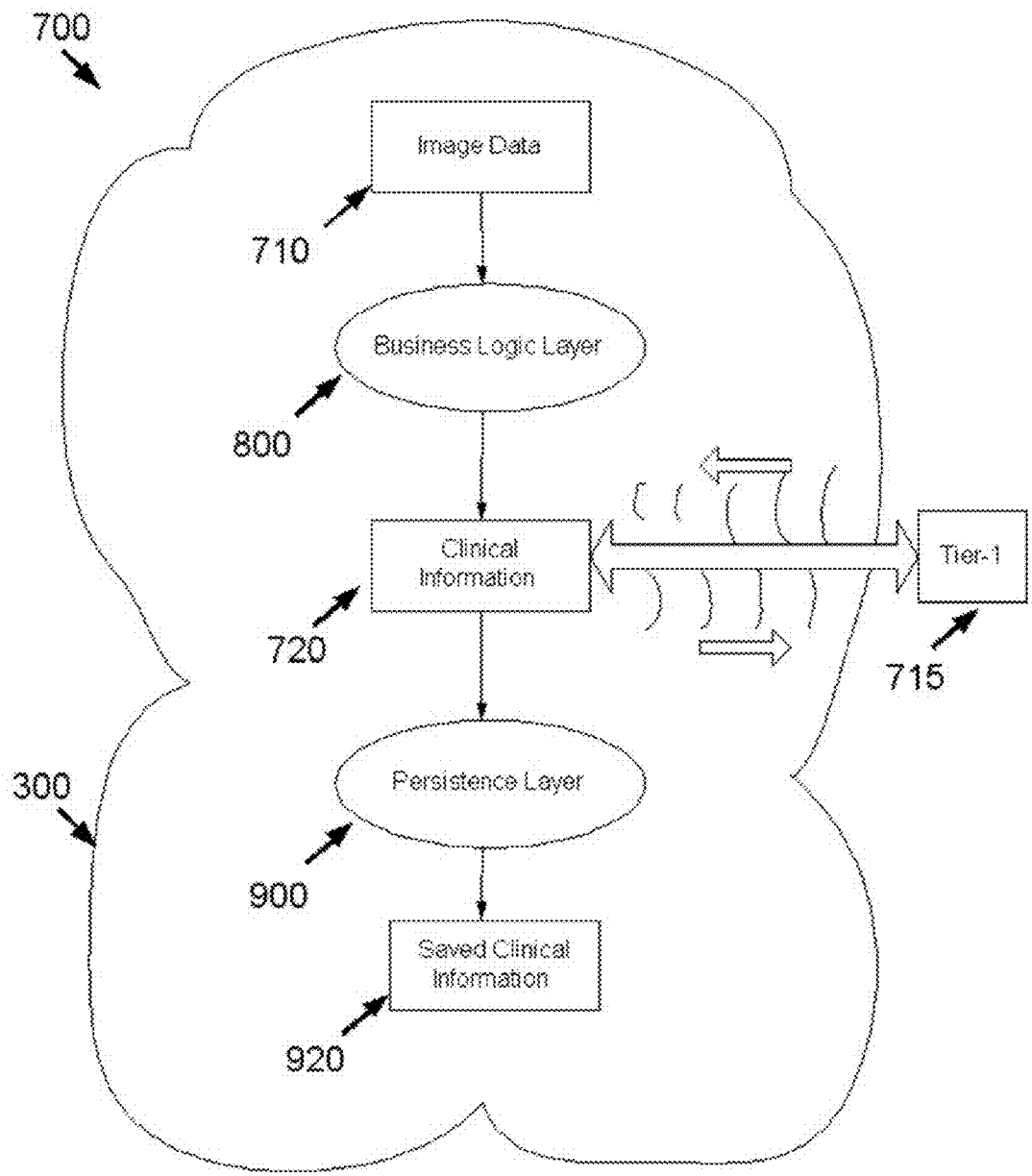
FIG. 3 shows an illustrative example of business layer and persistence layer combined on a cloud.

FIG. 3 shows the example embodiment 700, where the Cloud 300 hosts the Business Layer 800 and Persistence Layer 900. The image data is present in the Cloud storage 710. When the Tier-1 presentation layer 715 interacts with the Cloud hosting the application having Tier-2 and Tier-3, then the Clinical information is generated by the Business Logic Layer 800. This Clinical information can be seen on the presentation layer 715. The persistence layer 900 has the data information which is saved for the application. This can be a database management system which stores the clinical information 920 by running the data mining application. Such a model is very suitable for diagnostic, treatment support and monitoring of the diseases. An example can be for cardiovascular risk application for (a) cardiovascular application (such as IMT measurement, IMTV measurement, Plaque Characterization for Symptomatic vs. Asymptomatic classification of plaque, Stroke Risk computation, and monitoring stroke risk); (b) prostate cancer application (such as benign vs. malignant prostate tissue classification or characterization for prostate cancer); (c) ovarian cancer tissue characterization and classification; or (d) thyroid cancer application (such as benign vs. malignant thyroid tissue classification or characterization for thyroid cancer); or (e) classification of liver tissue such as Fatty Liver Disease, such that it can process the B-mode ultrasound or RF-mode ultrasound images. Under cardiovascular risk, it can compute say the intima-media thickness for the distal wall for the common carotid artery of ultrasound. Along the same lines can be the lumen quantification or lumen segmentation of the common carotid artery ultrasound or any blood vessels. This model is applicable for CCA, brachial artery, aortic arch and peripheral artery. Those skilled in the art can use this application for other arterial systems. Such an application can be for any 2D or 3D application. Another application can be the image data 710 that can be in 3D format and business logic layer 800 can process the image data 710 to give the segmentation results 720 which are being display on the Tier-1 device 710. Those killed in the art can use an iPad, iPhone or Samsung hand held devices for display of the transformed images or segmented images. An example can be a 3D Thyroid image data mining system such as ThyroScan™.

Figure 4:
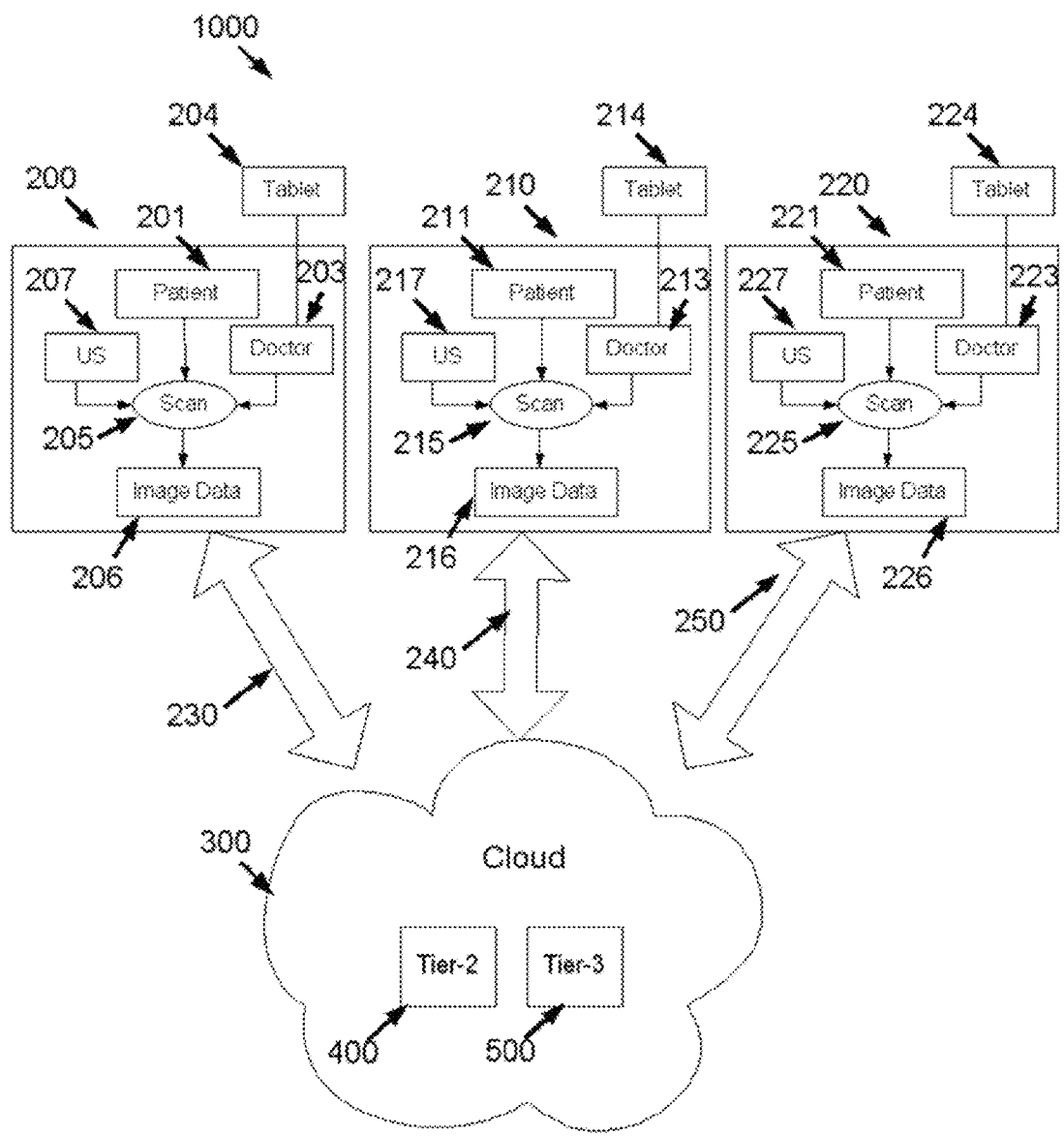
FIG. 4 shows an illustrative example of multi-tenancy approach with business layer and persistence layers in ultrasound framework.

FIG. 4 shows the example embodiment 1000, where the Cloud 300 hosts the Business Layer 400 and Persistence Layer 500. Health care system is represented by blocks 200, 210 and 220. The health care system 200 has the block 207 can be used as a body scanner says an ultrasound scanning system. Similarly, there can be another health care system 210 that has the scanner represented by the block 217. The embodiment 1000 also shows as an example where the third health care system is represented by 220 having the scanner block 227 and is an ultrasound scanning system. The ultrasound scanner can be a portable ultrasound scanner or an ultrasound scanner having a cart-based mobile in the hospital or health care system. The embodiment also shows the setup where the patient comes for scanning in the health care system. For example, patient block 201 shows the scanner 207 scanning the patient to generate the image data 206 in the healthcare system 200. Similarly, the embodiment also shows the setup where the patient block 211 shows the scanner 217 scanning the patient to generate the image data 216 in the healthcare system 210. Also shown are the wireless system 230, 240 and 250. Such an set-up can use for (a) cardiovascular application (such as IMT measurement, IMTV measurement, Plaque Characterization for Symptomatic vs. Asymptomatic classification of plaque, Stroke Risk computation, and monitoring stroke risk); (b) prostate cancer application (such as benign vs. malignant prostate tissue classification or characterization for prostate cancer); (c) ovarian cancer tissue characterization and classification; or (d) thyroid cancer application (such as benign vs. malignant thyroid tissue classification or characterization for thyroid cancer); or (e) classification of liver tissue such as Fatty Liver Disease.

Figure 5:
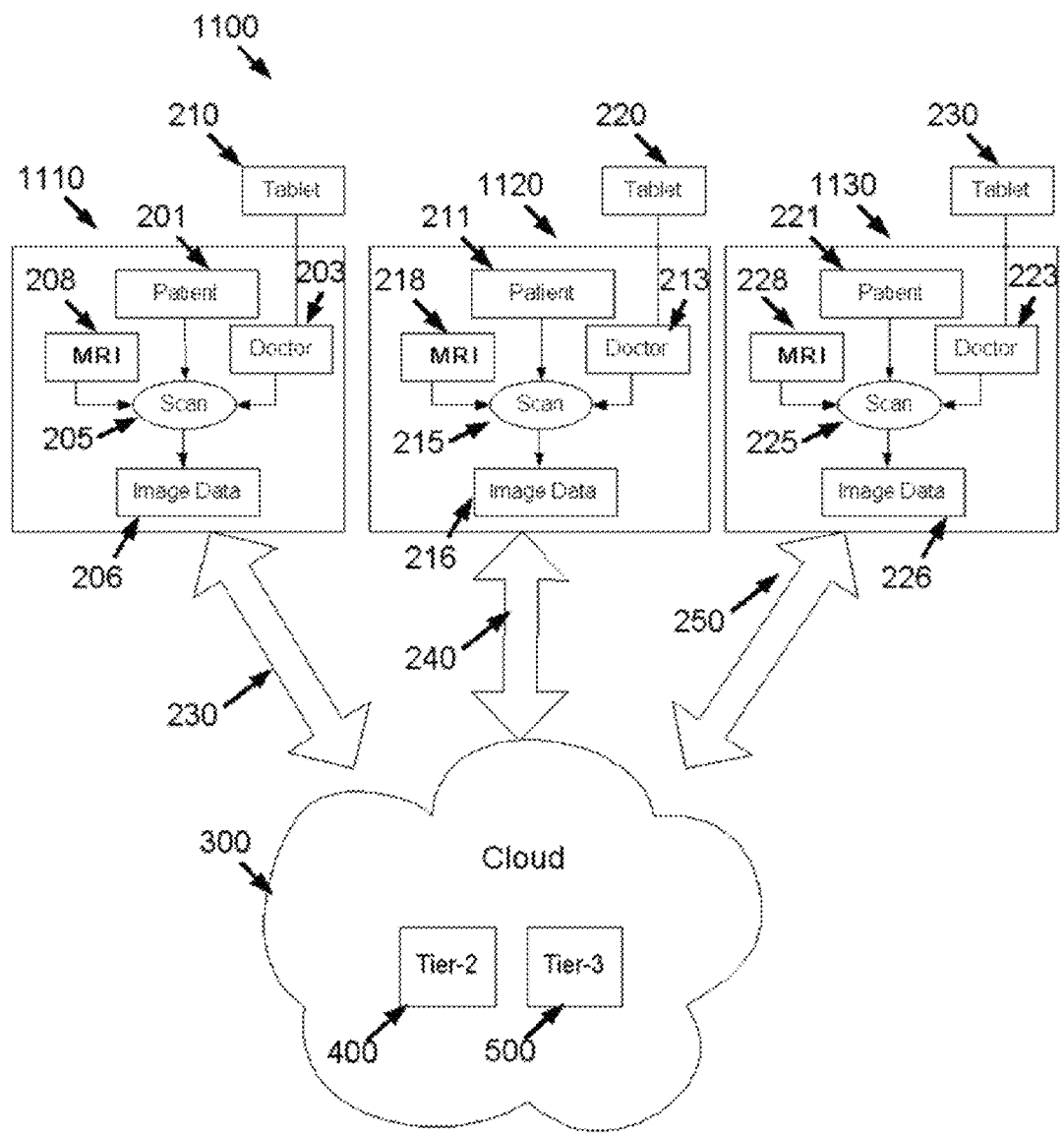
FIG. 5 shows an illustrative example of multi-tenancy approach with business layer and persistence layers in MR framework.

FIG. 5 shows the example embodiment 1100, where multiple tenants 1110, 1120 and 1130 are shown running the data mining application using Cloud 300 which hosts the Business Layer 400 and Persistence Layer 500. Tenant 1110 is the heath care system having the imaging device 208 such as MRI and the technologist or doctor 203 for scanning protocol 205 to yield the image data 206 for the patient 201. Similarly, there is a tenant 1120 is the heath care system having the imaging device 218 such as MRI and the technologist or doctor 213 for scanning protocol 215 to yield the image data 216 for the patient 211. Similarly, there is a tenant 1130 is the heath care system having the imaging device 228 such as MRI and the technologist or doctor 223 for scanning protocol 225 to yield the image data 226 for the patient 221. Also shown are the wireless system 230, 240 and 250. Such an set-up is used for (a) cardiovascular application (such as IMT measurement, IMTV measurement, Plaque Characterization for Symptomatic vs. Asymptomatic classification of plaque, Stroke Risk computation, and monitoring stroke risk); (b) prostate cancer application (such as benign vs. malignant prostate tissue classification or characterization for prostate cancer); (c) ovarian cancer tissue characterization and classification; or (d) thyroid cancer application (such as benign vs. malignant thyroid tissue classification or characterization for thyroid cancer); or (e) classification of liver tissue such as Fatty Liver Disease.

Figure 6:
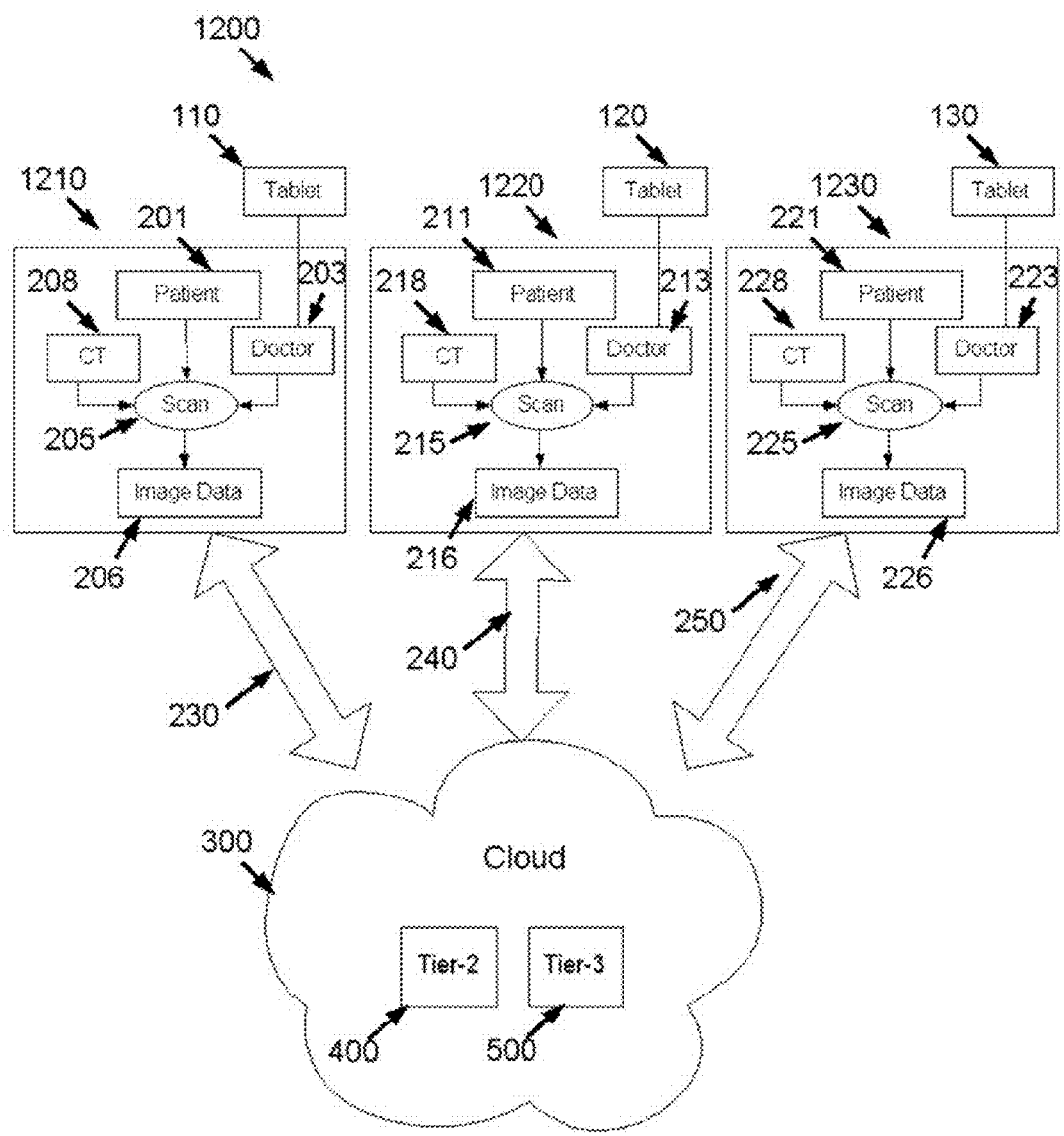
FIG. 6 shows an illustrative example of multi-tenancy approach with business layer and persistence layers in CT framework.

FIG. 6 shows the example embodiment 1200, where multiple tenants 1210, 1220 and 1230 are shown running the data mining application using Cloud 300 which hosts the Business Layer 400 and Persistence Layer 500. Tenant 1210 is the heath care system having the imaging device 208 such as CT and the technologist or doctor 203 for scanning protocol 205 to yield the image data 206 for the patient 201. Similarly, there is a tenant 1220 is the heath care system having the imaging device 218 such as CT and the technologist or doctor 213 for scanning protocol 215 to yield the image data 216 for the patient 211. Similarly, there is a tenant 1230 is the heath care system having the imaging device 228 such as CT and the technologist or doctor 223 for scanning protocol 225 to yield the image data 226 for the patient 221. Also shown are the wireless system 230, 240 and 250. Such an set-up is used for (a) cardiovascular application (such as IMT measurement, IMTV measurement, Plaque Characterization for Symptomatic vs. Asymptomatic classification of plaque, Stroke Risk computation, and monitoring stroke risk); (b) prostate cancer application (such as benign vs. malignant prostate tissue classification or characterization for prostate cancer); (c) ovarian cancer tissue characterization and classification; or (d) thyroid cancer application (such as benign vs. malignant thyroid tissue classification or characterization for thyroid cancer); or (e) classification of liver tissue such as Fatty Liver Disease.

Figure 7:
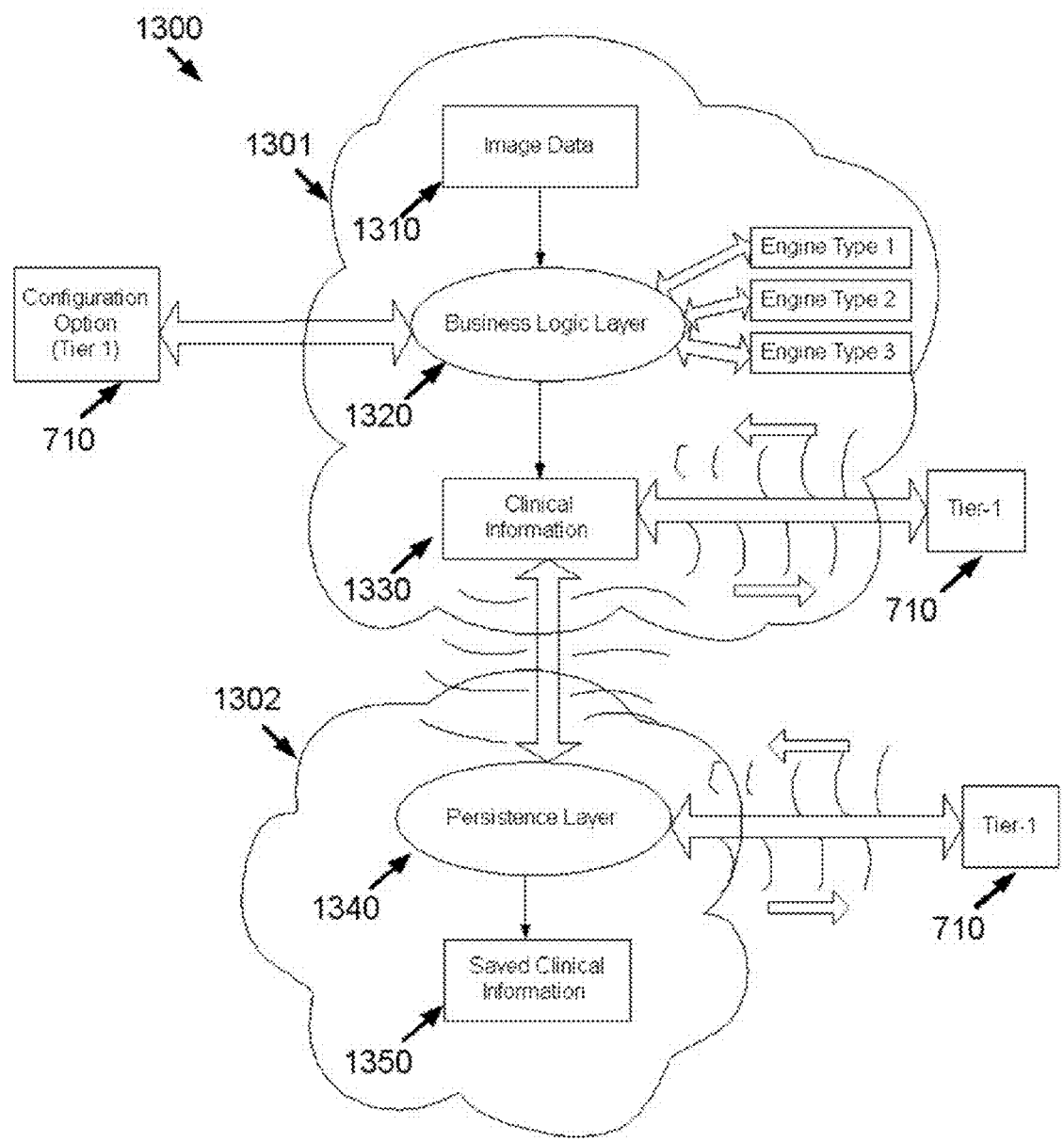
FIG. 7 shows an illustrative example of configuration options from presentation layer for a cloud-based setting.

FIG. 7 shows the example embodiment 900 showing different configuration options from presentation layer for a cloud-based setting. Business Logic Layer 800 received the image data from the tenant using the wireless system, which in turn processes the clinical information and gives the output 920. The configuration option 810, 820 and 830 are available for choosing the different types of engines such as Scientific Engine Type 1, Scientific Engine Type 2 or Scientific Engine Type 3. Tier 1, 710 can interact with the clinical information 920 to display the clinical diagnosis on 710, such as iPhone, iPad, Samsung Table, or even laptop, notebook or Desktop-based display devices. The persistence layer process 1000 processes the clinical information 920 and stores in the persistence layer. This information can also be accessed by Tier-1, 710. Output 930 is the information which is saved in the cloud or local server.

Figure 8:
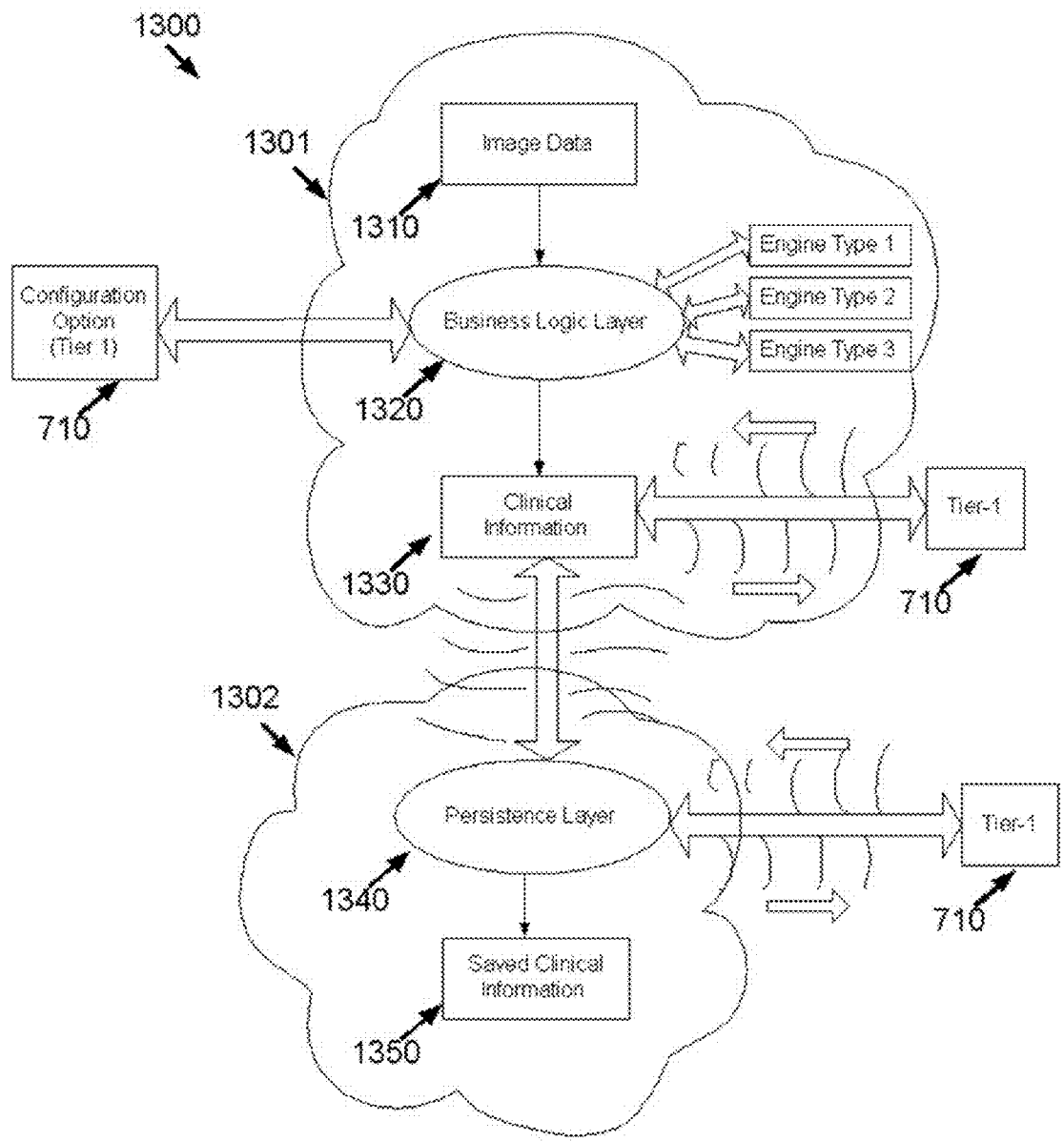
FIG. 8 shows an illustrative example of multiple clouds demonstrating the components of the applications hosted by different clouds.

FIG. 8 shows the example embodiment 1300 showing different configuration options from presentation layer for a cloud-based setting. Business Logic Layer 1320 receives the image data from the tenant using the wireless system, which in turn processes the clinical information and gives the output 1330. The configuration option is available for choosing the different types of engines such as Scientific Engine Type 1, Scientific Engine Type 2 or Scientific Engine Type 3. Tier 1, 710 can interact with the clinical information 1330 to display the clinical diagnosis on 710, such as iPhone, iPad, Samsung Table, or even laptop, notebook or Desktop-based display devices. The persistence layer process 1340 processes the clinical information 1330 and stores in the persistence layer. This information can also be accessed by Tier-1, 710. Output 1350 is the information which is saved in the cloud or local server. It is important to note that Persistence layer 1340 and clinical data results 1350 are stored in the cloud 1302 while Business Layer 1320 and the clinical information results 1330 are stored in the cloud 1301. Even though the entire data mining application is responding from the presentation layer 710, but the rest of the components are partitioned in different clouds using wireless operations. The data mining business layer can be applied for cardiovascular risk assessment, stroke risk assessment, liver disease assessment, vascular imaging assessment such as IMT measurement using AtheroEdge™ (source: Important systems like CAMES, CALEX, CALSFORM, CARES, CMUDS has been recently adapted. These methods are discussed in detail in: (a) Molinari F, Liboni W, Giustetto P, Badalamenti S, Suri J S. Automatic computer-based tracings (ACT) in longitudinal 2-D ultrasound images using different scanners. Journal of Mechanics in Medicine and Biology. 2009; 9:481-505; (b) Molinari F, Meiburger K M, Zeng G, Acharya U R, Liboni W, Nicolaides A, Suri J S. Carotid artery recognition system: A comparison of three automated paradigms for ultrasound images. Med Phys. 2012; 39:378; (c) Molinari F, Pattichis C, Zeng G, Saba L, Acharya U, Sanfilippo R, et al. Completely Automated Multi-resolution Edge Snapper (CAMES) inverted question mark A New Technique for an Accurate Carotid Ultrasound IMT Measurement: Clinical Validation and Benchmarking on a Multi-Institutional Database. IEEE Trans Image Process., 2012; (d) Molinari F, Krishnamurthi G, Acharya R U, Sree S V, Zeng G, Saba L, et al. Hypothesis validation for far wall brightness in carotid artery ultrasound for feature-based IMT measurement using combination of level set segmentation & registration. IEEE Trans Instrumentation & Measurement, 2012); plaque characterization using Atheromatic™ (source: Atheromatic™: symptomatic vs. asymptomatic classification of carotid ultrasound plaque using a combination of HOS, DWT & texture., Conf Proc IEEE Eng Med Biol Soc. 2011; 2011:4489-92), stroke risk assessment using AtheroRisk™, atherosclerosis disease monitoring using Atherometer™, Vessel Analysis using VesselOmeasure™, fatty liver disease characterization using Symptosis™ (source: Acharya et al., Data Mining Framework for Fatty Liver Disease Classification in Ultrasound: A Hybrid Feature Extraction Paradigm, Medical Physics, 2012) or tissue characterization for prostate using UroImage™ or benign vs. malignant tissue characterization using ThyroScan™ (source: ThyroScreen system: High resolution ultrasound thyroid image characterization into benign and malignant classes using novel combination of texture and discrete wavelet transform, Comput Methods Programs Biomed. 2011) or benign vs. malignant tissue characterization using GyneScan™. An example of the Symptosis™ system (source as: Archarya et al. Data Mining Framework for Fatty Liver Disease Classification in Ultrasound: A Hybrid Feature Extraction Paradigm, Medical Physics, 2012).

Figure 9:
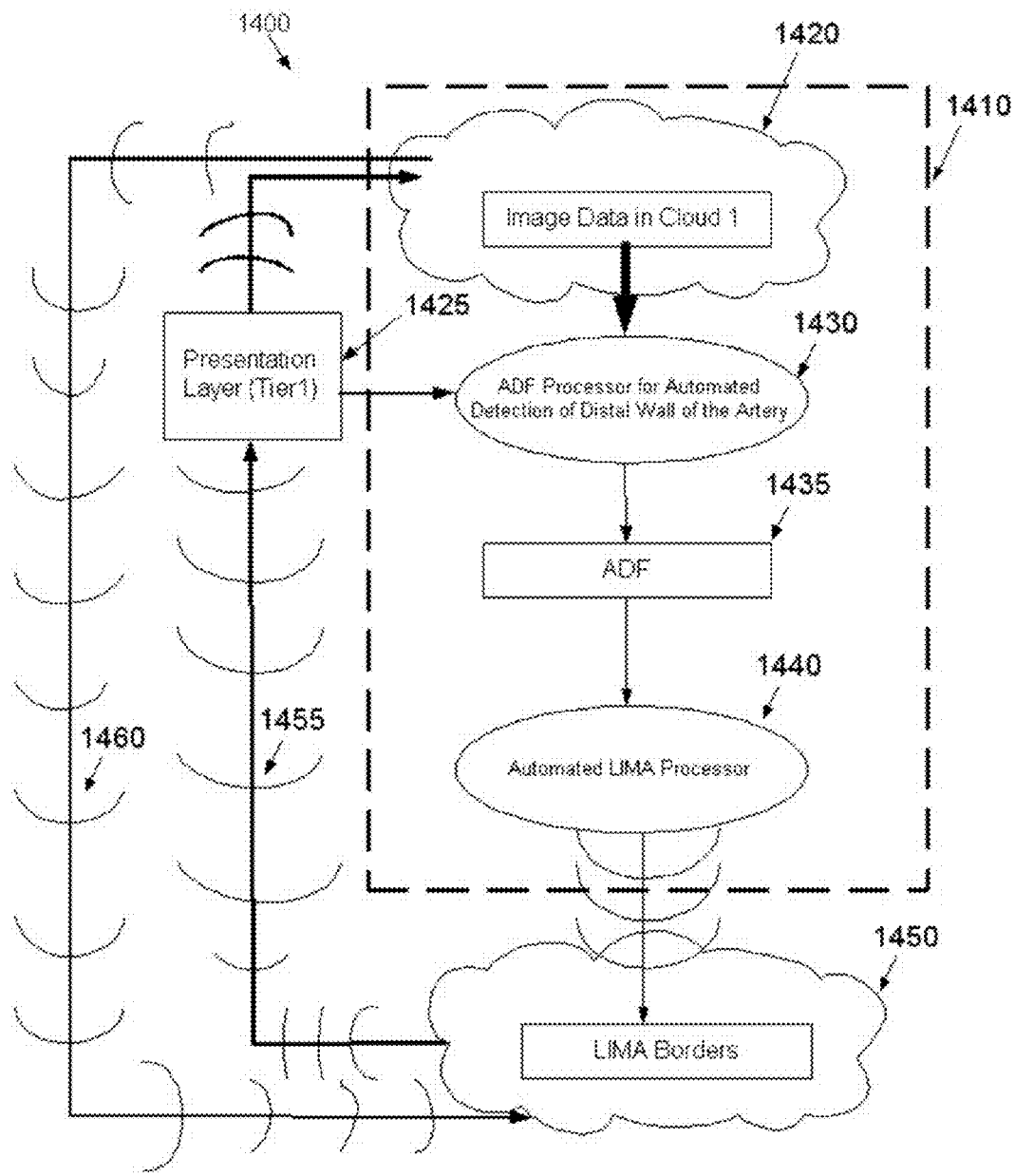
FIG. 9 shows an illustrative example of business logic and persistence layers for AtheroCloud™ application for carotid, brachial, femoral and aortic arch arterial ultrasound image.

FIG. 9 shows the example embodiment 1400 showing the automated system for IMT measurement in distributed mobile architecture framework. The Business layer is shown in dotted line in block 1410. Inside this block are two processors 1430 and 1440. Processor 1430 is the stage 1 of the IMT measurement system where far adventitia borders are recognized using multi-resolution framework developed by Molinari et al. (Completely Automated Multiresolution Edge Snapper—A New Technique for an Accurate Carotid Ultrasound IMT Measurement: Clinical Validation and Benchmarking on a Multi-Institutional Database, IEEE Transactions in Image Processing, Vol. 21, No. 3, March 2012). Block 1435 shows the output ADF (Far adventitia borders). Processor 1440 is the automated LIMA detection system using DoG filter driven by the automated multi-resolution framework for region of interest determination. The LIMA borders are then stored in the Persistence Layer in Cloud 2 (block 1450). Along with the LIMA border is the image 1460 sent wirelessly to the Cloud 2 block 1450. Presentation Layer 1425 fetches the LIMA borders from Cloud 1450 along the gray-scale image onto the Presentation Layer 1425. Such a system is the CAMES system as developed in the source (Molinari et al. Completely Automated Multiresolution Edge Snapper-A New Technique for an Accurate Carotid Ultrasound IMT Measurement: Clinical Validation and Benchmarking on a Multi-Institutional Database, IEEE Transactions in Image Processing, Vol. 21, No. 3, March 2012). The automated system 1430 and 1440 can also be replaced by CALEX system developed at the source Molinari et al, An Integrated Approach to Computer-Based Automated Tracing and Its Validation for 200 Common Carotid Arterial Wall Ultrasound Images, J Ultrasound Med 2010; 29:399-418. Another system can be the usage of constrained deformable model for stage 2 while keeping stage 1 as ADF processor. This system can be seen by Molinari et al. (source: Constrained Snake vs. Conventional Snake for Carotid Ultrasound automated IMT measurement on Multi-center data sets, Ultrasonix, 2012). Another system which is used for stage 1 and stage 2 for the blocks 1430 and 1440 using the system CAILRS developed by Molinari et al. (source: Automated carotid artery intima layer regional Segmentation, Phys. Med. Biol. 56 (2011) 4073-4090). Another system called CAUDLES can be used for blocks 1430 and block 1440 (source: Carotid Automated Ultrasound Double Line Extraction System Using Edge Flow, IEEE EMBS, 2012).

The AtheroEdge™ processor used CALEX, CAMES, CARES, CALSFORM, CMUDS systems for computing the LI/MA interfaces and then computing the CIMT values. These methods are discussed in detail in: (a) Molinari F, Liboni W, Giustetto P, Badalamenti S, Suri J S. Automatic computer-based tracings (ACT) in longitudinal 2-D ultrasound images using different scanners. Journal of Mechanics in Medicine and Biology. 2009; 9:481-505; (b) Molinari F, Meiburger K M, Zeng G, Acharya U R, Liboni W, Nicolaides A, Suri J S. Carotid artery recognition system: A comparison of three automated paradigms for ultrasound images. Med Phys. 2012; 39:378; (c) Molinari F, Pattichis C, Zeng G, Saba L, Acharya U, Sanfilippo R, et al. Completely Automated Multi-resolution Edge Snapper (CAMES) inverted question mark A New Technique for an Accurate Carotid Ultrasound IMT Measurement: Clinical Validation and Benchmarking on a Multi-Institutional Database. IEEE Trans Image Process., 2012; (d) Molinari F, Krishnamurthi G, Acharya R U, Sree S V, Zeng G, Saba L, et al. Hypothesis validation for far wall brightness in carotid artery ultrasound for feature-based IMT measurement using combination of level set segmentation & registration. IEEE Trans Instrumentation & Measurement, 2012.

Figure 10:
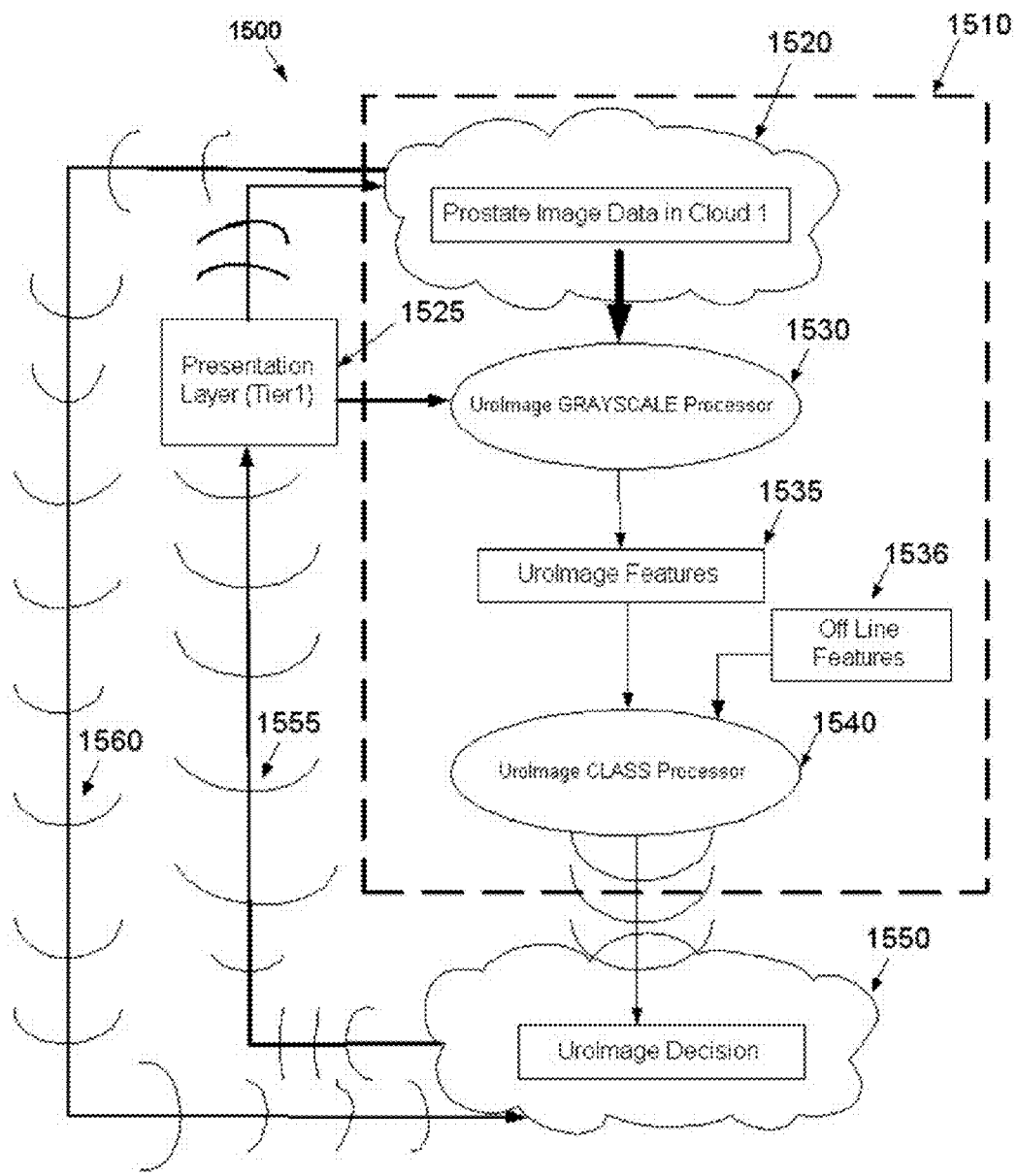
FIG. 10 shows an illustrative example of business logic and persistence layers for Cloud-based application for prostate benign vs. malignant cancer diagnoses using ultrasound image.

FIG. 10 show the example embodiment 1500 for the prostate cancer classification between benign prostate and malignant prostate using the cloud-based architecture. Block 1510 is the business layer shown in dotted line. The image data is shown using the block 1520. UroImage™ Grayscale Processor 1530 processes the prostate image data and generates the online features 1535 for the prostate. UroImage™ Class Processor 1540 is then used along with the offline features 1536 to generate the binary indicator in the persistence layer 1550. Note that the UroImage™ Decision are saved in the Cloud 1550. The presentation layer 1525 (a hand held device such as iPad or iPhone or Samsung Galaxy Tablet) is used to display the cancer prostate cancer information wirelessly using 1555. The image can also be retried on the presentation device from the cloud 1520. The image can also be saved from the Cloud 1520 to Cloud 1550 in the persistence layer. Thus the UroImage™ application for diagnosis and monitoring the cancer information of the prostate using a cloud-based application can use such a set-up.

Figure 11:
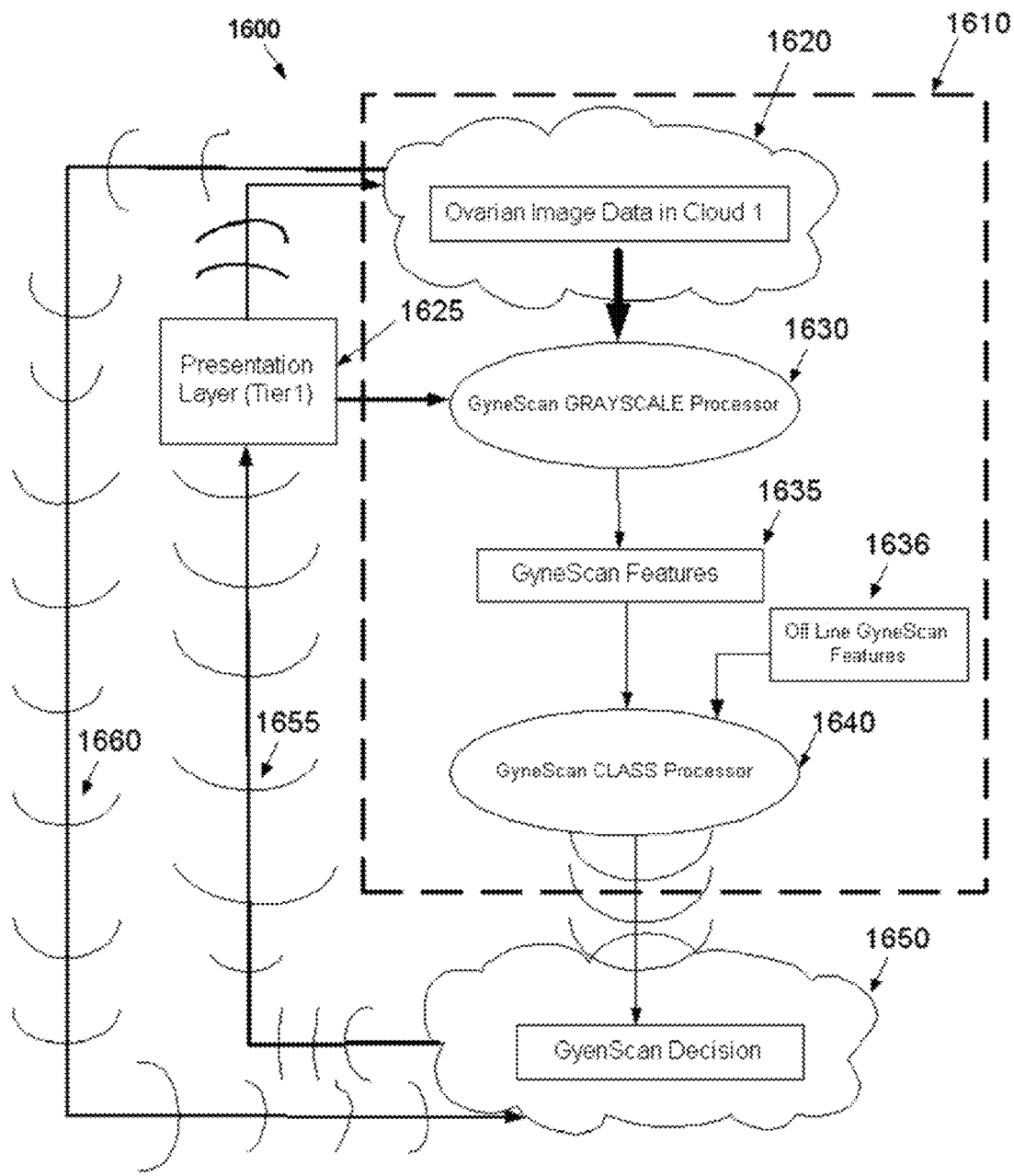
FIG. 11 shows an illustrative example of business logic and persistence layers for Cloud-based application for ovarian benign vs. malignant cancer diagnoses using ultrasound image.

FIG. 11 show the example embodiment 1600 for the ovarian cancer classification between benign ovarian and malignant ovarian using the cloud-based architecture. Block 1610 is the business layer shown in dotted line. The image data is shown using the block 1620. GyneScan™ Grayscale Processor 1630 processes the ovarian image data and generates the online features 1635 for the ovary. GyneScan™ Class Processor 1640 is then used along with the offline features 1636 to generate the binary indicator in the persistence layer 1650. Note that the GyneScan™ Decision are saved in the Cloud 1650. The presentation layer 1625 (a hand held device such as iPad or iPhone or Samsung Galaxy Tablet) is used to display the cancer ovary cancer information wirelessly using 1655. The image can also be retried on the presentation device from the cloud 1620. The image can also be saved from the Cloud 1620 to Cloud 1650 in the persistence layer. Thus the GyneScan™ application for diagnosis and monitoring the cancer information of the ovary using a cloud-based application can use such a set-up.

Figure 12:
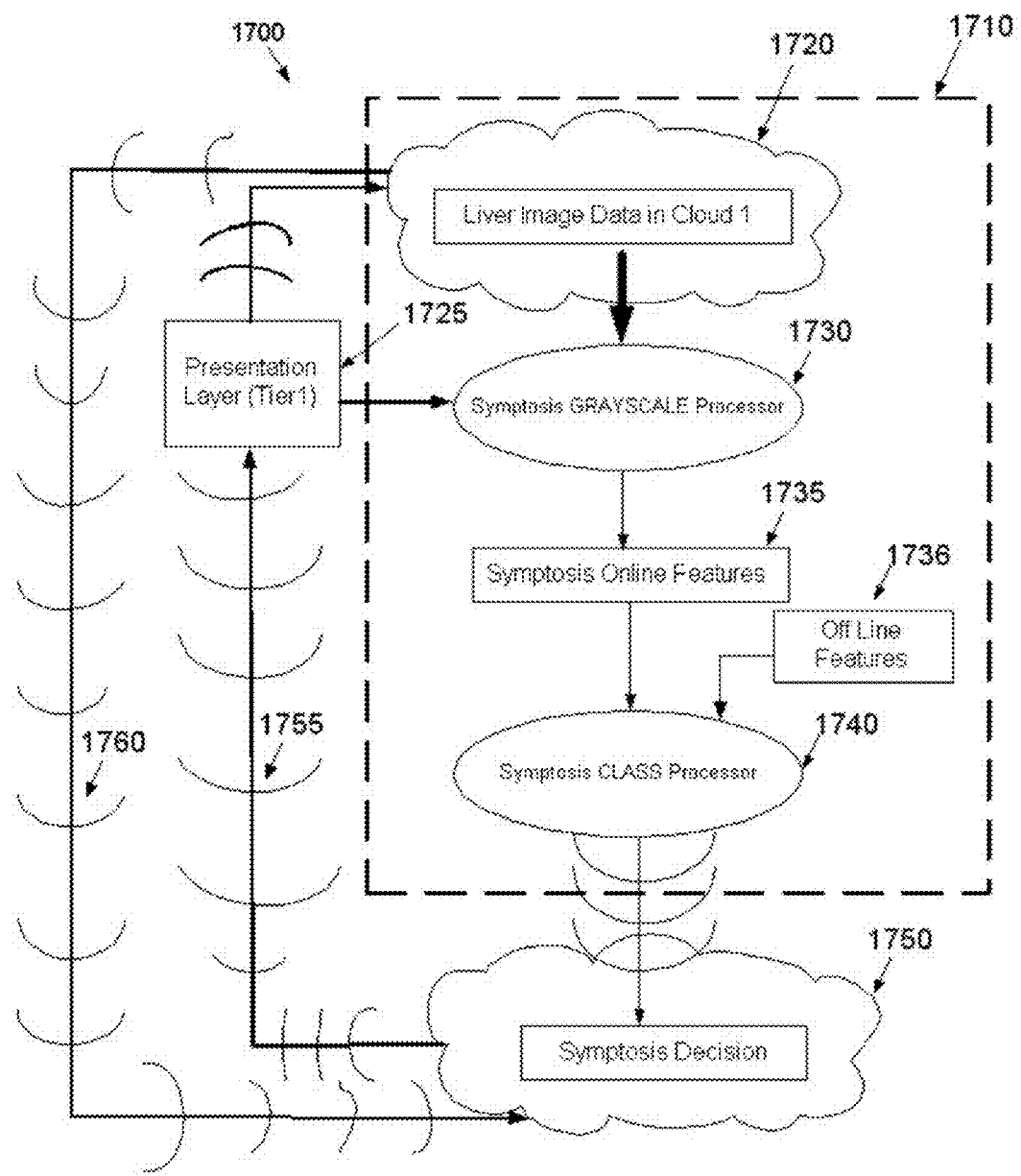
FIG. 12 shows an illustrative example of business logic and persistence layers for Cloud-based application for Fatty Liver Disease (FLD) diagnoses using ultrasound image.

FIG. 12 show the example embodiment 1700 for the fatty liver disease (FLD) vs normal liver classification the cloud-based architecture. Block 1710 is the business layer shown in dotted line. The image data is shown using the block 1720. Symptosis™ Grayscale Processor 1730 processes the liver ultrasound image data and generates the online features 1735 for the liver. Symptosis™ Class Processor 1740 is then used along with the offline features 1736 to generate the binary indicator in the persistence layer 1750. Note that the Symptosis™ Decision are saved in the Cloud 1750. The presentation layer 1725 (a hand held device such as iPad or iPhone or Samsung Galaxy Tablet) is used to display the FLD decision information wirelessly using 1755. The image can also be retried on the presentation device from the cloud 1720. The image can also be saved from the Cloud 1720 to Cloud 1750 in the persistence layer. Thus the Symptosis™ application for diagnosis and monitoring the FLD information in a cloud-based application can use such a set-up.

Figure 13:
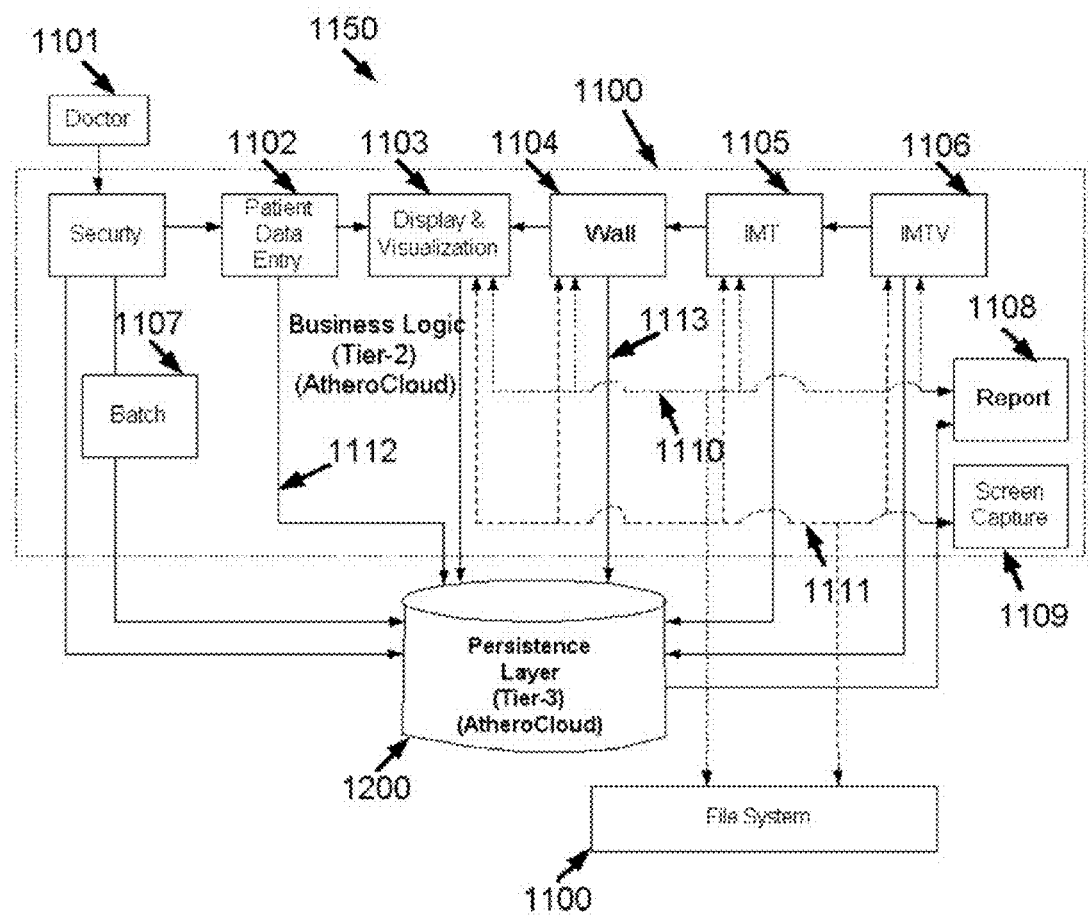
FIG. 13 shows an illustrative example of business logic and persistence layers for AtheroCloud™ application for carotid, brachial, femoral and aortic arch arterial ultrasound IMT measurement using two stage processes.

FIG. 13 show the example embodiment 1150 shows the interaction of the business layer and persistence layer 1200. This embodiment is an example for demonstration of IMT measurement using AtheroEdge™ software system. The Business Layer is composed of patient data entry 1102 using the security system. This security system output goes to the Persistence layer 1200 (called as AtheroCloud™). The patient data entry 1102 can be entered through the Tier-1 which finally goes to the Persistence Layer 1200. Note that 1112 can be wireless connected or hard wired on local or remote server. Block 1103 shows the display process but this information is on the Tier-1 on the presentation layer such as iPhone, iPad, Samsung Galaxy Tablet. All processing are displayed to the 1103. Block 1105 computes the Intima-Media Thickness (IMT) using AtheroEdge™ Business layer. Block 1106 computes the IMT variability a very important measure of cerebrovascular symptomaticity indicator for stroke risk. The output of the Wall Segmentation Engine of AtheroEdge™ is transferred to Persistence Layer 1200 via the wireless mode 1113 or hardwired mode. Note that the embodiment of 1150 can be implemented in one cloud setting or multiple cloud settings. FIG. 7 is the example of one cloud setting while the FIG. 8 is the two cloud settings. If it is one cloud setting then the connection 1113 is implemented using a hard wired system and if it is multiple cloud setting, then 1113 is wireless. Block 1108 is the report generation box which helps generate the patient's report in Tier-2. The report is saved in Tier-3 and there is a arrow connecting one-way from Persistence Layer to the Report Display. Block 1108 pull data from the Persistence Layer and generates the report and display on the display and visualization unit (Tier-1). Note that 1108 is run in Business layer while fetching the data from the Persistence Layer in another Cloud. Block 1109 is the Screen Capture, which allows capturing the screen at any time and is part of the Business Layer. Screen Capture gets display at block 1103. Block 1107 allows running the batch processing on a set of carotid ultrasound image using AtheroEdge™ system. The results of the batch are stored in the Persistence Layer 1200. The innovation about this application is that Tier-1 allows running the batch of images which are present in the first Cloud while the batch is being processed in Tier-2 and the results of the batch are being stored in Tier-3. This allows distributed process of medical imaging data mining systems. This takes full advantages of speed and efficient sharing of the data bases. The block 1100 is the file system.

Figure 14:
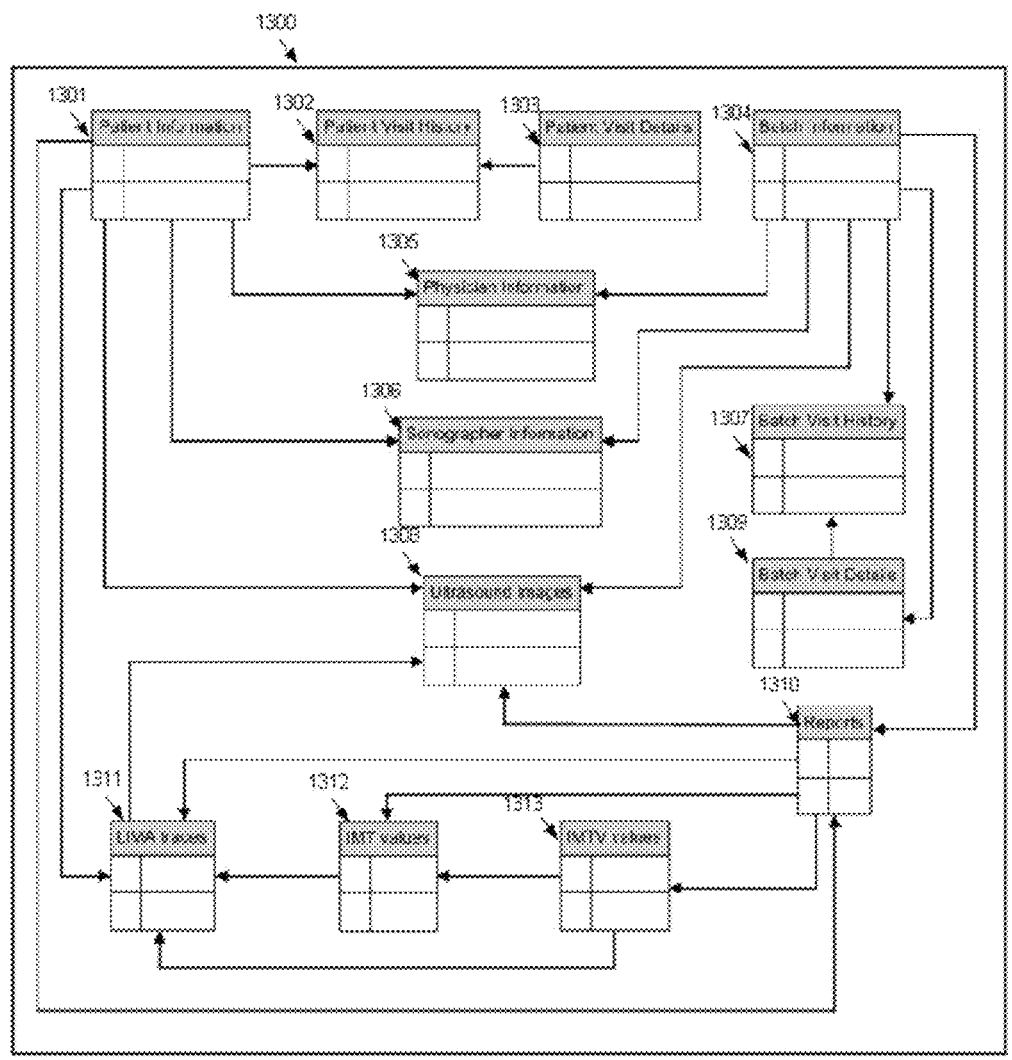
FIG. 14 shows an illustrative example of persistence layer table for AtheroMobile™ application using AtheroCloud™.

FIG. 14 shows the example embodiment 1300 showing the table concept for an image-based data mining application (AtheroMobile™) using the Cloud Concept. Block 1301 shows the patient information which is connected to block 1311 LI/MA borders for the distal wall of the carotid artery for the AtheroEdge™ application. Block 1310 picks up the ultrasound images from block 1308 and LI/MA profiles (the list of x,y coordinate points) 1311 and generates the report 1310. Report 1310 also picks the IMT values 1312 and IMTV values 1313 to add in the report. This is the case of running one image at a time. When the batch run is made the report statistics is generated which grabs batch information 1304, ultrasound images 1308, IMT values from 1312, IMTV values 1313, LI/MA profiles or borders 1311. Block 1310 report also accepts the patient information from 1301. Physician information 1305 and Sonographer information 1306 is connected for both single case 1301 processing of image and processing of the batch cases 1304. Block 1307 shows the batch history, telling the time when the batch was run, who ran the batch, ID of the batch and batch related attributes.

Figure 15:
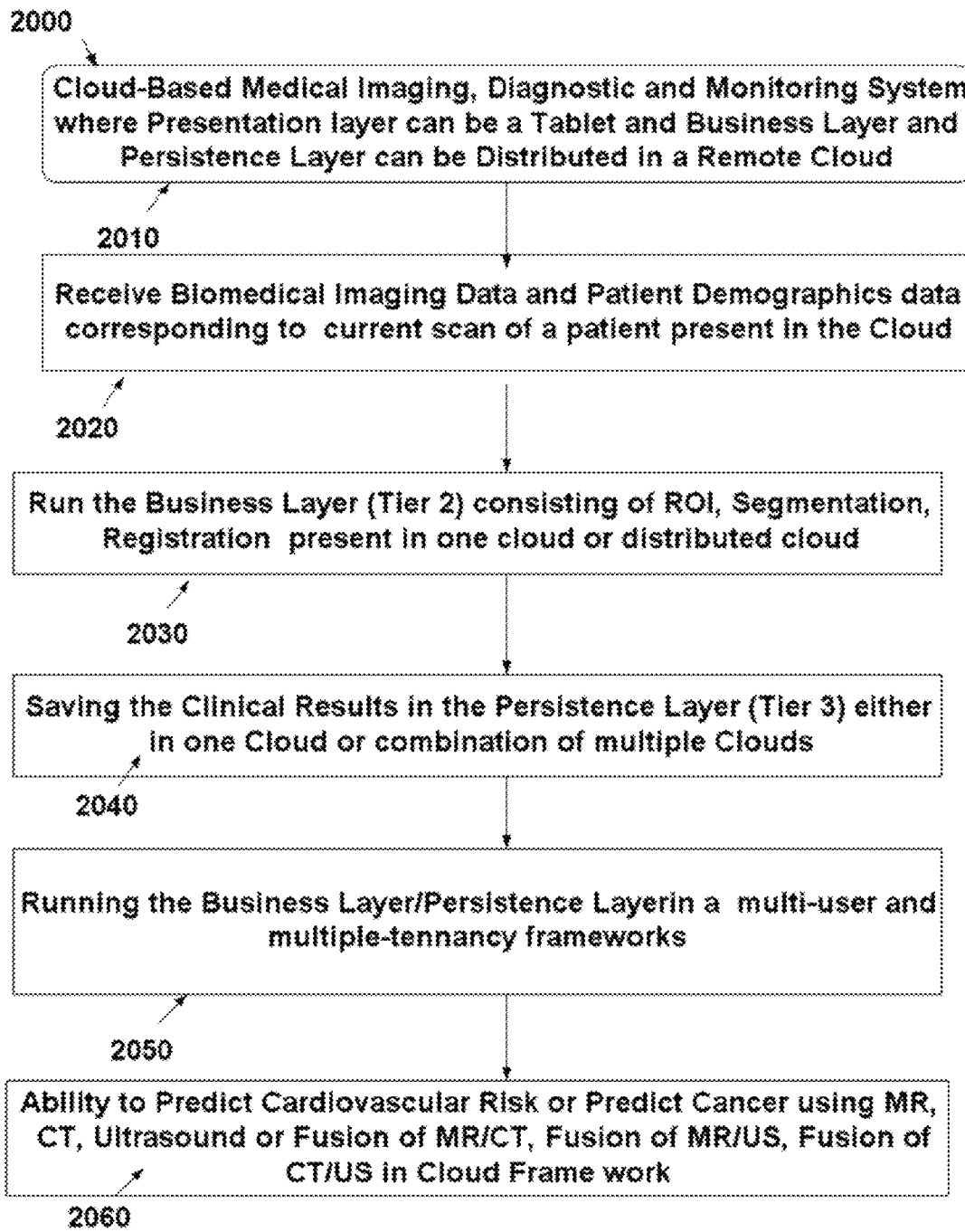
FIG. 15 shows the overall view of the system.

FIG. 15 shows the example embodiment 2000 of the data mining application. Data mining application 2010 using single Clouds or a set of Clouds which consist of Tier-1 as a presentation layer, Tier-2 is the business layer and Tier-3 is the Persistence Layer. The set-up 2010 is used for diagnostic and monitoring application. The Presentation Layer in data mining framework for cardiovascular risk assessment, stroke risk assessment, liver disease assessment, vascular imaging assessment such as IMT measurement using AtheroEdge™, plaque characterization using Atheromatic™, stroke risk assessment using AtheroRisk™, atherosclerosis disease monitoring using Atherometer™, Vessel Analysis using VesselOmeasure™, fatty liver disease characterization using Symptosis™, tissue characterization for prostate using UroImage™ or image-based Alzheimer's disease assessment. Block 2020 receives the image data from the Cloud for processing. Block 2030 runs the business layer and Block 2040 is the Persistence Layer for the application. Block 2050 is the block where the application can use multiple tenancy-multi user frame work. Block 2060 show the application using multiple image-based setting such as MR, CT, Ultrasound or its fusion.

Figure 16:
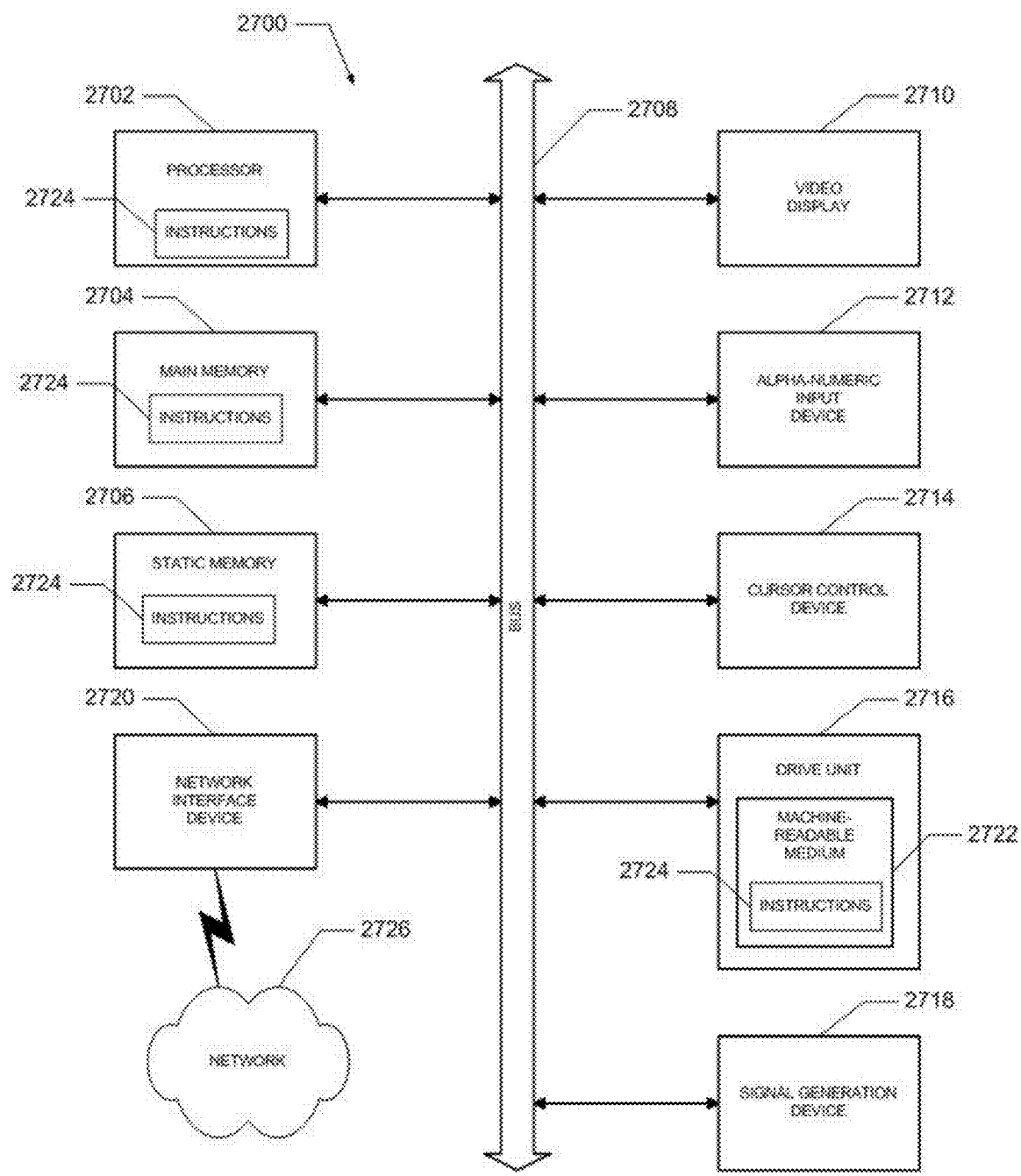
FIG. 16 shows a diagrammatic representation of machine in the example form of a computer system within which a set of instructions when executed may cause the machine to perform any one or more of the methodologies discussed herein.

FIG. 16 shows a diagrammatic representation of machine in the example form of a computer system 2700 within which a set of instructions when executed may cause the machine to perform any one or more of the methodologies discussed herein. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" can also be taken to include any collection of machines that individually or jointly execute a set (or multiple sets) of instructions to perform any one or more of the methodologies discussed herein.

The example computer system 2700 includes a processor 2702 (e.g., a central processing unit (CPU), a graphics processing unit (GPU), or both), a main memory 2704 and a static memory 2706, which communicate with each other via a bus 2708. The computer system 2700 may further include a video display unit 2710 (e.g., a liquid crystal display (LCD) or a cathode ray tube (CRT)). The computer system 2700 also includes an input device 2712 (e.g., a keyboard), a cursor control device 2714 (e.g., a mouse), a disk drive unit 2716, a signal generation device 2718 (e.g., a speaker) and a network interface device 2720.

The disk drive unit 2716 includes a machine-readable medium 2722 on which is stored one or more sets of instructions (e.g., software 2724) embodying any one or more of the methodologies or functions described herein. The instructions 2724 may also reside, completely or at least partially, within the main memory 2704, the static memory 2706, and/or within the processor 2702 during execution thereof by the computer system 2700. The main memory 2704 and the processor 2702 also may constitute machine-readable media. The instructions 2724 may further be transmitted or received over a network 2726 via the network interface device 2720. While the machine-readable medium 2722 is shown in an example embodiment to be a single medium, the term "machine-readable medium" should be taken to include a non-transitory single medium or multiple media (e.g., a centralized or distributed database, and/or associated caches and servers) that store the one or more sets of instructions. The term "machine-readable medium" can also be taken to include any medium that is capable of storing, encoding or carrying a set of instructions for execution by the machine and that cause the machine to perform any one or more of the methodologies of the various embodiments, or that is capable of storing, encoding or carrying data structures utilized by or associated with such a set of instructions. The term "machine-readable medium" can accordingly be taken to include, but not be limited to, solid-state memories, optical media, and magnetic media.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A computer-implemented method comprising:
receiving image data on a mobile presentation device, such as hand-held device having a display screen, from a current image of a patient record stored in a network cloud;
using a data processor in data communication with a business layer (tier 2) containing a data mining application in the cloud;
using the data processor in data communication with the business layer (tier 2) containing an automated data mining application in the cloud with several configurations for creating multiple business layers or fusion of business layers;
using the data processor in data communication with a persistence layer (tier 3) containing an automated data mining application in network communication with the business layer;
displaying the processed results on the presentation layer computed by the automated data mining application and computed using a combination of business layer and a persistence layer;
using the data processor in data communication with a presentation layer (tier-1) displaying the processed results computed by the automated data mining application and computed using a combination of business layer and a persistence layers, and able to communicate between presentation layer, business layer and persistence layer of the three tier architecture; and
computing a cardiovascular risk, stroke risk, computing diagnostic index for benign vs. malignant tissue for ovarian cancer diagnosis, computing diagnostic index for benign vs. malignant tissue for prostate cancer diagnosis, computing diagnostic index for benign vs. malignant tissue for thyroid cancer diagnosis, and computing the classification index for liver images for diagnosis of fatty liver disease.

2. The method as claimed in claim 1 which can be used for diagnosis or monitoring of cardiovascular risk by computing the intima media thickness (AtheroEdge).

3. The method as claimed in claim 1 which can be used for diagnosis or monitoring of cardiovascular risk by computing the symptomatic risk (Atheromatic).

4. The method as claimed in claim 1 which can be used for diagnosis or monitoring of cardiovascular risk by linking the HbA1c Diabetic Index with Intima Media Thickness (AtheroEdgeLink).

5. The method as claimed in claim 1 which can be used for diagnosis or monitoring of cardiovascular risk by linking the Syntax Score computed from coronary angiography (CAG) with Intima Media Thickness and prediction of coronary artery disease (AtheroEdgeLink).

6. The method as claimed in claim 1 which can be used for diagnosis or monitoring of prostate Cancer Risk by computing the benign vs. malignant cancer index (UroImage).

7. The method as claimed in claim 1 which can be used for diagnosis or monitoring of Ovarian Cancer Risk by computing the benign vs. malignant cancer index (GyneScan).

8. The method as claimed in claim 1 which can be used for diagnosis or monitoring of Liver Cancer Disease by computing the classification index for Fatty Liver Disease (Symptosis).

9. The method as claimed in claim 2 where the Business layer (tier 2) can be an ultrasound B-mode data or an RF mode ultrasound data set.

10. The method as claimed in claim 1 where the Business layer (tier 3) can receive the MR data.

11. The method as claimed in claim 1 where the Business layer (tier 3) can be a CT data.

12. The method as claimed in claim 1 where the set-up of presentation layer (tier-1) is a hand-held device, a laptop or notebook or a desktop or an iPhone or a tablet and receives data from Business Layer and Persistence Layers using the controls of Presentation Layer.

13. The method as claimed in claim 1 where the set-up of business layer (tier-2) can be in one cloud and persistence layer (tier-3) can be in same or another cloud, so called distributed cloud architecture by splitting the different tiers of the architecture for computing a cardiovascular risk, stroke risk, computing diagnostic index for benign vs. malignant tissue for ovarian cancer diagnosis, computing diagnostic index for benign vs. malignant tissue for prostate cancer diagnosis, computing diagnostic index for benign vs. malignant tissue for thyroid cancer diagnosis, and computing the classification index for liver images for diagnosis of fatty liver disease.

14. The method as claimed in claim 2 where the set-up of business layer (tier-2) can have several configurations controlled by the presentation layer (tier 1)—such configurations can be using different techniques for data mining using CALEX, CAMES, CALSFORM, CAILRS, CMUDS.

15. The method as claimed in claim 1 where the set-up uses a wireless system for data transfer between the presentation layer and business layer and vice-versa.

16. The method as claimed in claim 1 where the set-up uses a wireless system for data transfer between the presentation layer and persistence layers and vice-versa.

17. The method as claimed in claim 2 where the set-up of presentation layer (tier-1), business layer (tier-2) and persistence layer (tier-3) can be used for IMT measurement (AtheroEdge™) for Carotid, Brachial, Femoral and Aortic Arch blood vessel arterial images.

18. The method as claimed in claim 2 where the set-up of presentation layer (tier-1), business layer (tier-2) and persistence layer (tier-3) can be used for stroke risk (AtheroRisk™) assessment.

19. The method as claimed in claim 1 where the business layer can be utilize any 2D or 3D segmentation engine for quantification of lesions or monitoring the lesions over time having several configurations (scientific engines) or fusion of different configurations.

20. The method as claimed in claim 1 where the business layer can be utilize any 2D or 3D segmentation engine for quantification method based on training-based systems.

* * * * *